(12) United States Patent
Nakao et al.

(10) Patent No.: US 6,303,628 B1
(45) Date of Patent: Oct. 16, 2001

(54) BICYCLICCARBONYL INDOLE COMPOUNDS AS ANTI-INFLAMMATORY/ ANALGESIC AGENTS

(75) Inventors: Kazunari Nakao; Shigeo Hayashi; Rodney W. Stevens, all of Chita-Gun (JP)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/605,811

(22) Filed: Jun. 28, 2000

Related U.S. Application Data

(63) Continuation of application No. PCT/IB99/01243, filed on Jul. 2, 1999.

(51) Int. Cl.⁷ .................... C07D 401/06; C07D 209/18; A61K 31/404
(52) U.S. Cl. .................. 514/307; 514/314; 514/414; 514/415; 546/146; 546/168; 548/454; 548/469
(58) Field of Search .................... 546/135, 146, 546/168; 548/454, 469; 514/307, 314, 415

(56) References Cited

U.S. PATENT DOCUMENTS

| | | | |
|---|---|---|---|
| 5,284,862 | * 2/1996 | Bigge et al. | 514/419 |
| 5,436,265 | 7/1995 | Black et al. | 514/420 |
| 5,510,368 | * 4/1996 | Lau et al. | 514/419 |

FOREIGN PATENT DOCUMENTS

| | | |
|---|---|---|
| 9709308 | 3/1997 | (WO) . |
| 9905104 | 2/1999 | (WO) . |
| 9935130 | 7/1999 | (WO) . |

OTHER PUBLICATIONS

European Search Report, 2000.

* cited by examiner

Primary Examiner—Zinna Northington Davis

(74) Attorney, Agent, or Firm—Peter C. Richardson; Paul H. Ginsburg; Elsa Djuardi

(57) ABSTRACT

This invention provides a compound of the following formula:

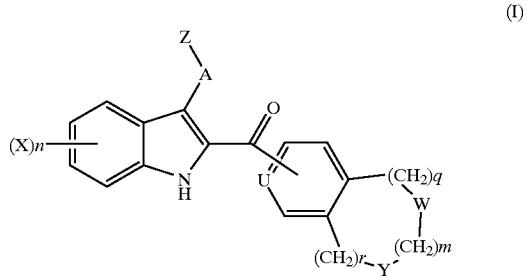

(I)

or the pharmaceutically acceptable salts thereof wherein A is $C_{1-6}$ alkylene or $-NR^1-$; Z is $C(=L)R^2$, or $SO_2R^3$; U is CH or N; W and Y are independently selected from $-CH_2-$, O, S and $-N-R^1$; m is 1, 2 or 3; q and r are independently 0, 1 or 2; X is independently selected from halogen, $C_{1-4}$ alkyl, halo-substituted $C_{1-4}$ alkyl, hydroxy, $C_{1-4}$ alkoxy, halo-substituted $C_{1-4}$ alkoxy or the like; n is 1 or 2; L is oxygen or sulfur; $R^1$ is hydrogen or $C_{1-4}$ alkyl; $R^2$ is hydroxy, $C_{1-6}$alkyl, halo-substituted $C_{1-6}$ alkyl, $C_{1-6}$ alkoxy, halo-substituted $C_{1-6}$ alkoxy, $C_{3-7}$ cycloalkoxy, $C_{1-4}$ alkyl($C_{3-7}$ cycloalkoxy), $-NR^4R^5$ or the like; $R^3$ is $C_{1-6}$ alkyl or halo-substituted $C_{1-6}$ alkyl; and $R^4$ and $R^5$ are independently selected from hydrogen, $C_{1-6}$ alkyl and halo-substituted $C_{1-6}$alkyl.

This invention also provides a pharmaceutical composition useful for the treatment of a medical condition in which prostaglandins are implicated as pathogens.

12 Claims, No Drawings

BICYCLICCARBONYL INDOLE COMPOUNDS AS ANTI-INFLAMMATORY/ANALGESIC AGENTS

This application is a continuation of PCT/IB99/01243 filed Jul. 2, 1999.

Technical Field

This invention relates to bicycliccarbonyl indoles as pharmaceutical agents. This invention specifically relates to compounds, compositions and methods for the treatment or alleviation of pain, inflammation, other inflammation-associated disorders such as arthritis, and the like in humans, dogs, cats and the like.

BACKGROUND ART

Nonsteroidal antiinflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.;Willoughby, D. A. *Proc. Natl. Acad. Sci. USA*, 1994, 91, 2046). COX-1 is thought to play a physiological role and to be responsible for gastrointestinal and renal protection. On the other hand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, nepbrotoxicity, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme cyclooxygenase-2 and/or by intervention of the activity of the enzyme cyclooxygenase-2 on arachidonic acid would provide alternate therapy to the use of NSAIDs or corticosteriods in that such compounds would exert anti-inflammatory effects without the adverse side effects associated with COX-1 inhibition.

A variety of indole compounds are known and are disclosed in several patent applications. International Publication Number WO 96/32379 discloses N-substituted indole compounds as cGMP-PDE Inhibitors. International Publication Numbers WO 96/37467, WO 96/37469, UK Patent Publication GB 2283745 A and U.S. Pat. No. 5,510,368 disclose 2-methyl-N-substituted indole compounds as cyclooxygenase-2 Inhibitors. Also, a variety of indole compounds are disclosed as agents for controlling underwater fouling organisms in European Patent Publication Number 0 556 949 A2. International Publication Number WO 99/05104 discloses 3-amino-substituted indole compounds. Further, International Publication Number WO 97/09308 discloses indole compounds as neuropeptide receptor antagonists.

BRIEF DISCLOSURE OF THE INVENTION

The present invention provides a compound of the following formula:

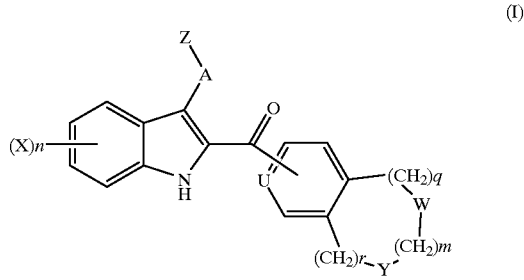

(I)

or the pharmaceutically acceptable salts thereof wherein

A is $C_{1-6}$ alkylene or $-NR^1-$;

Z is $C(=L)R^2$, or $SO_2R^3$;

U is CH or N;

W and Y are independently selected from $-CH_2-$, O, S and $-N-R^1$;

m is 1, 2 or 3;

q and r are independently 0, 1 or 2;

X is independently selected from halogen, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino and cyano;

n is 0, 1, 2, 3 or 4;

L is oxygen or sulfur;

$R^1$ is hydrogen or $C_{1-4}$ alkyl;

$R^2$ is hydroxy, $C_{1-6}$ alkyl, halo-substituted $C_{1-6}$ alkyl, $C_{1-6}$ alkoxy, halo-substituted $C_{1-6}$ alkoxy, $C_{3-7}$ cycloalkoxy, $C_{1-4}$ alkyl($C_{3-7}$ cycloalkoxy), $-NR^4R^5$, $C_{1-4}$ alkylphenyl-O— or phenyl-O—, said phenyl being optionally substituted with one to five substituents independently selected from halogen, $C_{1-4}$ alkyl, hydroxy, $C_{1-4}$ alkoxy and nitro;

$R^3$ is $C_{1-6}$ alkyl or halo-substituted $C_{1-6}$ alkyl; and $R^4$ and $R^5$ are independently selected from hydrogen, $C_{1-6}$ alkyl and halo-substituted $C_{1-6}$ alkyl.

The indole compounds of the present invention exhibit inhibition of COX activity. Preferably compounds of this invention exhibit inhibitory activity against COX-2, with more preferable compounds having COX-2 selectivity.

Accordingly, the present invention also provides a pharmaceutical composition, useful for the treatment of a medical condition in which prostaglandins are implicated as pathogens, which comprises a compound of the formula (I) and the pharmaceutically acceptable salts thereof.

Further, the present invention also provides compounds which can be used as intermediates of formula (I) where in A is methylene;

Z is $C(=O)OCH_3$;

U is CH or N;

W and Y are independently selected from —CH$_2$—, O and N—R$^1$;

m is 1, or 2;

q and r are independently 0 or 1;

X is independently selected from chloro, trifluoromethyl, and methoxy;

n is 1 or 2; and

R$^1$ is hydrogen or methyl.

Further, the present invention provides a method for the treatment of a medical condition in which prostaglandins are implicated as pathogens, in a mammalian subject, dog, cat etc. which comprises administering to said subject a therapeutically effective amount of said pharmaceutical composition.

The medical conditions in which prostaglandins are implicated as pathogens, include the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease (osteoarthritis), gout, ankylosing spondylitis, systemic lumpus erythematosus and juvenile arthritis, bursitis, burns, injuries following surgical and dental procedures.

The compounds and pharmaceutical composition of this invention may inhibit cellular neoplastic transformations and metastatic tumor growth and thus may be used in the treatment and/or prevention of cancers in the colon, breast, skin, esophagus, stomach, urinary bladder, lung and liver. The compounds and pharmaceutical composition of this invention were used in the treatment and/or prevention of cyclooxygenase-mediated proliferation disorders such as which occur in diabetic retinopathy and tumor angiogenesis.

The compounds and pharmaceutical composition of this invention may inhibit prostaniod-induced smooth muscle contraction by preventing the synthesis of contractile prostanoids, and thus may be of use in the treatment of dysmenorrhea, premature labor, asthma and eosinophil related disorders and in the treatment of neurodegenerative diseases such as Alzheimer's and Parkinson's disease, and for the treatment of bone loss (treatment of osteoarthritis), stroke, seizures, migraine, multiple sclevosis, AIDS and encephaloathy.

By virtue of the COX-2 activity and/or specificity for COX-2 over COX-1, such compounds will prove useful as an alternative to conventional NSAIDs particularly where such NSAIDs may be contra-indicated such as in patients with ulcers (such as peptic ulcers and gastric ulcers), gastritis, regional enterotis, ulcerative colitis, diverticulitis or with a recurrent history of GI lesions, GI bleeding, coagulation disorders including anemia such as hypoprothrombinemia, hemophilia and other bleeding problems; kidney disease; prior to surgery of taking of anticoagulants.

DETAILED DISCLOSURE OF THE INVENTION

As used herein, the term "halo" means fluoro, chloro, bromo or iodo.

As used herein, the term "C$_{1-6}$ alkyl" means straight or branched chain saturated radicals of 1 to 6 carbon atoms, including, but not limited to methyl, ethyl, n-propyl, isopropyl, n-butyl, isobutyl, sec-butyl, tert-butyl, pentyl, hexyl and the like.

As used herein, the term "alkylene" means saturated hydrocarbon (straight chain or branched) wherein a hydrogen atom is removed from each of the terminal carbons such as methylene, ethylene, propylene, butylene, pentylene, hexylene and the like.

As used herein, the term "halo-substituted alkyl" means an alkyl radical as described above substituted with one or more halogens included, but not limited to, chloromethyl, dichloromethyl, fluoromethyl, difluoromethyl, trifluoromethyl, 2,2,2-trichloroethyl and the like.

As used herein, the term "C$_{3-7}$ cycloalkyl" means carbocyclic radicals, of 3 to 7 carbon atoms, including, but not limited to cyclopropyl, cyclobutyl, cyclopentyl, cyclohexyl, cycloheptyl and the like.

Examples of "alkoxy" are methoxy, ethoxy, n-propoxy, isopropoxy, n-butoxy, isobutoxy, sec-butoxy, tert-butoxy and the like.

Examples of "alkylthio" are methylthio, ethylthio, n-propylthio, isopropylthio, n-butylthio, isobutylthio, sec-butylthio, tert-butylthio and the like.

Examples of "mono-(C$_{1-4}$ alkyl)amino" are methylamino, ethylamino, n-propylamino, isopropylamino, n-butylamino, isobutylamino, sec-butylamino, tert-butylamino and the like.

Examples of "di-(C$_{1-4}$ alkyl)amino" are dimethylamino, diethylamino, dipropylamino, N-methyl-N-ethylamino, N-methyl-N-propylamino, N-methyl-N-butylamino, N-ethyl-N-propylamino and the like.

Examples of "HO-(C$_{1-4}$)alkyl" are hydroxymethyl, hydroxyethyl (e.g., 1-hydroxyethyl and 2-hydroxyethyl), hydroxypropyl (e.g., 1- hydroxypropyl, 2-hydroxypropyl and 3-hydroxypropyl).

Examples of "C$_{1-4}$ alkoxy-C$_{1-4}$ alkyl" are methoxymethyl, methoxyethyl, methoxypropyl, methoxybutyl, ethoxymethyl, ethoxyethyl, ethoxypropyl and the like.

Examples of "halo-substituted alkoxy" are chloromethoxy, dichloromethoxy, fluoromethoxy, difluoromethoxy, trifluoromethoxy, 2,2,2-trichloroethoxy and the like.

Examples of "aryl" are phenyl, naphthyl and the like.

Examples of the group of the following formula:

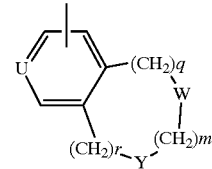

are tetralinyl, 5,6,7,8,-tetrahydroisoquinolinyl, 2,3-dihydro-1,4-benzodioxinyl, 2,3-dihydro-1-benzofuranyl, 1,3-benzodioxolyl, indanyl, 1,2,3,4-tetrahydroquinolinyl, 2,3-dihydro-1H-indolyl, 1,2,3,4-tetrahydroisoquinolinyl, chromanyl, isochromanyl, isoindolinyl, 2,3-dihydrofuro[3,2-c]pyridinyl, 1,2,3,4-tetrahydropyrido[3,4-b]pyrazinyl, 1,2,3,4-tetrahydro[2,6]naphthyridinyl, 3,4-dihydro-1H-pyrano[3,4-c]pyridinyl, 1,2,3,4-tetrahydro[1,6]naphthyridinyl, 3,4-dihydro-2H-pyrano[3,2-c]pyridinyl, 1,2,3,4-tetrahydro[1,7]naphthyridinyl, 1,2,3,4-tetrahydro[2,7]naphthyridinyl, 3,4-dihydro-1H-pyrano[4,3-c]pyridinyl, 2,3-dihydro-1H-pyrrolo[3,2-c]pyridinyl, 2,3-dihydro-1H-pyrrolo[2,3-c]pyridinyl, 2,3-dihydrofuro[2,3-c]pyridinyl, 2,3-dihydro-1H-pyrrolo[3,4-c]pyridinyl, 1,3-dihydrofuro[3,4-c]pyridinyl, [1,3]dioxolo[4,5-c]pyridinyl, 3,4-dihydro-2H-pyrano[2,3-c]pyridinyl, 1,2,3,4-tetahydroquinoxalinyl, 2,3-dihydro-1- benzothienyl, 1,3-dihydro-2-benzothienyl, 1,3-benzodithiolyl, 2,3-dihydrothieno[2,3-c]pyridinyl, 1,3-dihydrothieno[3,4-c]pyridinyl, [1,3]dithiolo[4,5-c]pyridinyl, thiochromanyl, 3,4-dihydro-1H-isothiochromanyl, 2,3-dihydro-1,4-benzodithiinyl and the like. The ring nitrogen atom(s) in said group can be optionally substituted by $C_1$–$C_4$ alkyl, preferably methyl and ethyl.

Preferred compounds of this invention are those of the formula (I) wherein
- A is $C_{1-6}$ alkylene;
- Z is $C(=L)R^2$;
- U is CH or N;
- W and Y are independently selected from —$CH_2$—, O, S and —N—$R^1$;
- m is 1,2 or 3;
- q and r are independently 0, 1 or 2;
- X is independently selected from halogen, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino and cyano;
- n is 0, 1, 2 or 3;
- L is oxygen or sulfur;
- $R^1$ is hydrogen or $C_{1-4}$ alkyl;
- $R^2$ is hydroxy, $C_{1-6}$ alkoxy, halo-substituted $C_{1-6}$ alkoxy, $C_{3-7}$ cycloalkoxy, $C_{1-4}$ alkyl($C_{3-7}$ cycloalkoxy), —$NR^4R^5$, $C_{1-4}$ alkylphenyl-O— or phenyl-O—, said phenyl being optionally substituted with one to five substituents independently selected from halogen, $C_{1-4}$ alkyl, hydroxy, $C_{1-4}$ alkoxy and nitro; and
- $R^4$ and $R^5$ are independently selected from hydrogen, $C_{1-6}$ alkyl and halo-substituted $C_{1-6}$ alkyl.

Further preferred compounds of this invention are those of the formula
- A is $C_{1-4}$ alkylene;
- Z is $C(=O)R^2$;
- U is CH or N;
- W and Y are independently selected from —$CH_2$—, O and —N—$R^1$;
- m is 1 or 2;
- q and r are independently 0 or 1;
- X is independently selected from halogen, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino and cyano;
- n is 1 or 2;
- $R^1$ is hydrogen or $C_{1-4}$ alkyl; and
- $R^2$ is hydroxy, $C_{1-6}$ alkoxy, halo-substituted $C_{1-6}$ alkoxy, $C_{3-7}$ cycloalkoxy, $C_{1-4}$ alkyl($C_{3-7}$ cycloalkoxy), $C_{1-4}$ alkylphenyl-O— or phenyl-O—, said phenyl being optionally substituted with one to five substituents independently selected from halogen, $C_{1-4}$ alkyl, hydroxy, $C_{1-4}$ alkoxy and nitro;

Further preferred compounds of this invention are those of the formula (I) wherein
- A is methylene or ethylene;
- Z is $C(=O)R^2$;
- U is CH or N;
- W and Y are independently selected from —$CH_2$—, O and —N—$R^1$;
- m is 1 or 2;
- q and r are independently 0 or 1;
- X is independently selected from fluoro, chloro, $C_{1-4}$ alkyl, halo-substitutedmethyl, and methoxy;
- n is 1 or 2;
- $R^1$ is hydrogen or methyl; and
- $R^2$ is hydroxy or $C_{1-6}$ alkoxy;

with the proviso that at least one of U, W and Y is a hetero atom.

Further preferred compounds of this invention are those of the formula (I) wherein
- A is methylene;
- Z is $C(=O)OH$;
- U is CH or N;
- W and Y are independently selected from —$CH_2$—, O, and —N—$R^1$;
- m is 1, or 2;
- q and r are independently 0 or 1;
- X is independently selected from chloro, trifluoromethyl, and methoxy;
- n is 1 or 2; and
- $R^1$ is hydrogen or methyl.

Further preferred compounds of this invention are those of the formula (I) wherein
- A is methylene;
- Z is $C(=O)OH$;
- U is CH or N;
- W, Y, m, q and r are selected from the group consisting of
  a) W and Y are —$CH_2$—, m is 1, and q and r are independently 0 or 1;
  b) W and Y are —$CH_2$—, m is 2, and q and r are 0;
  c) W and Y are O, m is 1 or 2, and q and r are 0;
  d) W is —$CH_2$—, Y is O, m is 1, and q and r are 0;
  e) W is O, Y is —$CH_2$—, m is 1, and q and r are 0;
  f) W is —N—$R^1$, Y is —$CH_2$—, m is 1, and q and r are independently 0 or 1;
  g) W is —N—$R^1$, Y is —$CH_2$—, m is 2, and q and r are 0;
  h) W is —$CH_2$—, Y is —N—$R^1$, m is 1, and q and r are independently 0 or 1;
  i) W is —$CH_2$—, Y is —N—$R^1$, m is 2, and q and r are 0;
- X is independently selected from chloro, trifluoromethyl, and methoxy;
- n is 1 or 2; and
- $R^1$ is hydrogen or methyl.

Preferred individual compounds of this invention are:
[6-chloro-2-[(5,6,7,8-tetrahydroisoquinolin-3-yl)carbonyl]-1H-indol-3-yl]acetic acid;
[6-chloro-2-[(2,3-dihydro-1,4-benzodioxin-6-yl)carbonyl]-1H-indol-3-yl]acetic acid;
[2-[(2,3-dihydro-1,4-benzodioxin-6-yl)carbonyl]-5-trifluoromethyl-1H-indol-3-yl]acetic acid;
[6-chloro-2-[(2,3-dihydro-1-benzofuran-5-yl)carbonyl]-1H-indol-3-yl]acetic acid;
[2-[(1,3-benzodioxol-5-yl)carbonyl]-6-chloro-1H-indol-3-yl]acetic acid;
[5,6-dichloro-2-[(indan-5-yl)carbonyl]-1H-indol-3-yl]acetic acid;
[5-methoxy-2-[(1,2,3,4-tetrahydroquinolin-7-yl)carbonyl]-1H-indol-3-yl]acetic acid;
[5,6-dichloro-2-[(2,3-dihydro-1H-indol-5-yl)carbonyl]-1H-indol-3-yl]acetic acid; and
[6-chloro-2-[(2-methyl-1,2,3,4-tetrahydroisoquinolin-7-yl)carbonyl]-1H-indol-3-yl]acetic acid,
and a salt thereof.

Most preferred individual compounds are:
[6-chloro-2-[(5,6,7,8-tetrahydroisoquinolin-3-yl)carbonyl]-1H-indol-3-yl]acetic acid;

[6-chloro-2-[(2,3-dihydro-1,4-benzodioxin-6-yl)carbonyl]-1H-indol-3-yl]acetic acid;
[2-[(2,3-dihydro-1,4-benzodioxin-6-yl)carbonyl]-5-trifluoromethyl-1H-indol-3-yl]acetic acid; and [6-chloro-2-[(2,3-dihydro-1-benzofuran-5-yl)carbonyl]-1H-indol-3yl]acetic acid;
and a salt thereof.

Preferred individual compounds which can be used as intermediates of this invention are:

methyl [6-chloro-2-[(5,6,7,8-tetrahydroisoquinolin-3-yl)carbonyl]-1H-indol-3-yl]acetate;
methyl [6-chloro-2-[(2,3-dihydro-1,4-benzodioxin-6-yl)carbonyl]-1H-indol-3-yl]* acetate;
methyl [2-[(2,3-dihydro-1,4-benzodioxin-6-yl)carbonyl]-5-trifluoromethyl-1H-indol-3-yl]acetate;
methyl [6-chloro-2-[(2,3-dihydro-1-benzofuran-5-yl)carbonyl]-1H-indol-3-yl]acetate;
methyl [2-[(1,3-benzodioxol-5-yl)carbonyl]-6-chloro-1H-indol-3-yl]acetate;
methyl [5,6-dichloro-2-[(indan-5-yl)carbonyl]-1H-indol-3-yl]acetate; and
methyl [6-chloro-2-[(2-methyl-1,2,3,4-tetrahydroisoquinolin-7-yl)carbonyl]-1H-indol-3-yl] acetate,
and a salt thereof.

General Synthesis

A compound of general formula (I) may be prepared by any synthetic procedure applicable to structure-related compounds known to those skilled in the art. The following representative examples as described hereinafter are illustrative and are not meant to limit the scope of the invention in anyway. Unless otherwise stated, A, U, W, X, Y, Z, q, r, m, n, $R^1$, $R^2$, $R^3$, $R^4$ and $R^5$ are as defined herein before.

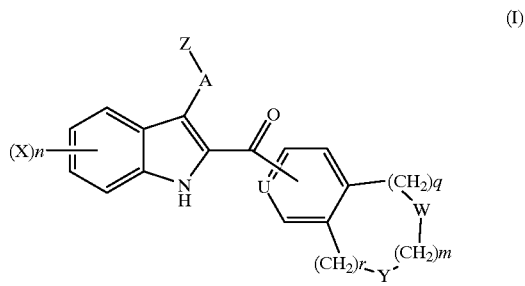

(I)

In one embodiment, for example, a compound of the formula (I) wherein A is —$CH_2$— and Z is $CO_2H$ may be prepared according to the reaction sequences depicted in Scheme 1.

Scheme 1

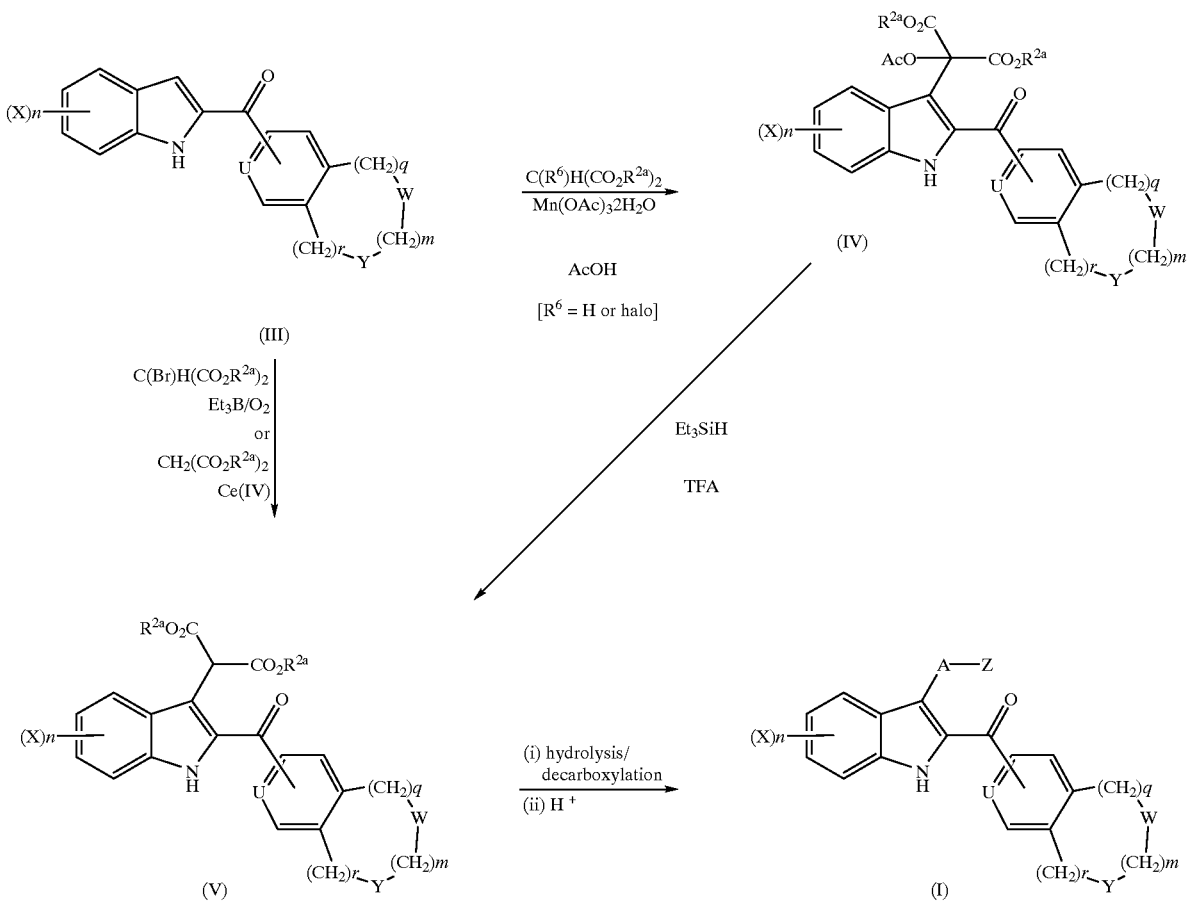

In brief, a compound of formula (III) is subjected to oxidative homolytic malonylation (for leading references see J. M. Muchowski et al; Can. J. Chem., 70, 1838, 1992 and E. Baciocchi et al; J. Org. Chem., 58, 7610, 1993). In one example, a compound of the formula (III) is reacted with a compound of the formula $C(R^6)H(CO_2R^{2a})_2$, wherein $OR^{2a}$ is $R^2$ and $R^6$ is hydrogen, or halogen, preferably chloro, and a manganese(III) agent, preferably manganese (III) triacetate. The manganese(III) agent is usually used in stoichiometric amounts but, alternatively, may be made catalytic by use of a suitable reoxidizing agent such as sodium persulfate, usually in the presence of a co-catalyst such as, a silver(I) salt such as silver nitrate. Preferred reaction solvent includes acetic acid, however, acetic acid—acetic anhydride or other protic solvents such as propionic acid can be used. The reaction is preferably conducted in the presence of sodium acetate or potassium acetate, but, may be conducted in solvent alone. Reaction temperatures are generally in the range of room temperature to reflux temperature of the solvent, preferably 60 to 100° C., but if necessary, lower or higher temperature can be employed. Reaction times are, in general, from one hour to a day, preferably from 4 to 16 hours, however shorter or longer reaction times, if necessary, can be employed. In the immediate instance, the α-acetoxy compounds of formula (IV) is usually obtained as the major product. Compounds of formula (IV) can readily be transformed to compounds of formula (V) by reduction with a suitable reducing agent, for example, a trialkylsilane, preferably triethylsilane in a suitable protic solvent, notably, trifluoroacetic acid. Alternatively, the reaction can be conducted in a reaction inert co-solvent such as dichloromethane or 1,2-dichloroethane, or the like. Reaction temperatures are generally in the range of room temperature to reflux temperature of the solvent, but if necessary, lower or higher temperature can be employed. Reaction times are, in general, from 1 minute to a day, preferably from 20 minutes to 5 hours, however shorter or longer reaction times, if necessary, can be employed. Alternatively, a compound of formula (V) may be obtained directly from a compound of formula (III) from a monohalomalonate of formula: $C(Br)H(CO_2R^{2a})_2$, preferably, bromomalonate, mediated by aerial oxidation of a trialkylborane such as triethylborane (see B. Giese; In Radicals in organic synthesis: formation of carbon-carbon bonds. Pergamon Press, Oxford pp. 86–89, 1986, and P. G. Allies and P. B. Brindley; J. Chem. Soc. (B), 1126, 1960) or, (ii) a malonic ester in the presence of a cerium(IV) salt such as cerium(IV) ammonium nitrate (for example, see E. Baciocchi et al; Tetrahedron Lett, 2763, 1986). A compound of formula (V) may be readily transformed to a compound of formula (VI) by subjection to saponification/decarboxlation under standard conditions.

Alternatively, as depicted in Scheme 2, a compound of the formula (I), wherein A is —$(R^7)$CH—, Z is $CO_2H$, and $R^7$ is $C_{1-5}$ alkyl, may be prepared in an analogous manner to that of described in Scheme 1 from a suitable monoalkylmalonate, $C(R^7)L^1(CO_2R^{2a})_2$, wherein $L^1$ is hydrogen or a halogen, preferably bromide, from a compound of formula (III).

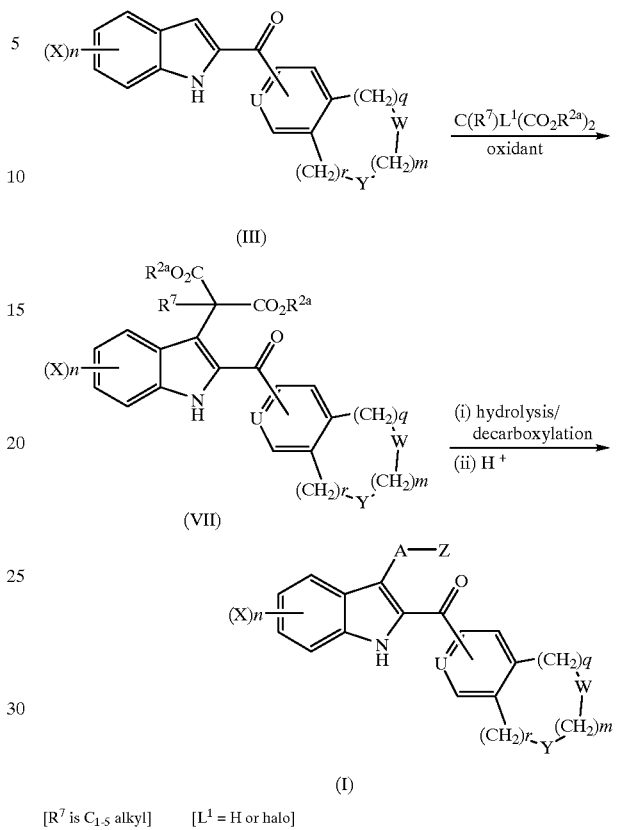

Scheme 2

[$R^7$ is $C_{1-5}$ alkyl]    [$L^1$ = H or halo]

In another embodiment, as depicted in Scheme 3, a compound of formula (I), wherein A is —$(R^8)$CH—, Z is $CO_2H$, and $R^8$ is hydrogen or $C_{1-5}$ alkyl, is readily accessible from the appropriate 2-aminocinnamic acid ester (IX) wherein $G^1$ is a suitable protecting group, for example, methoxycarbonyl, ethoxycarbonyl, tert-butoxycarbonyl (Boc), benzyloxycarbonyl, phenylsulfonyl or p-toluenesulfonyl, or the like. Thus, the requisite 2-aminocinnamic acid ester (IX) is reacted with a compound of formula (XI), wherein E is halogen, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, cesium carbonate, sodium hydride or potassium hydride. Preferred reaction inert solvents include, but are not limited to, acetone, methyl ethyl ketone, acetonitrile, N,N-dimethylformamide, N,N-dimethylacetamide, dimethylsulfoxide, dioxane or tetrahydrofuran. Reaction temperatures are preferably in the range of –40° C. to reflux temperature of the solvent, usually in the range of 0° C. to 60° C., but if necessary, lower or higher temperature can be employed. Reaction time is in general from 1 minute to a day, preferably from 30 minutes to 8 hours, however shorter or longer reaction times, if necessary, can be employed. When the reaction is, for example, con ducted at room temperature the intermediate indoline (X) can be isolated. Reaction at higher temperatures can result in formation of indole (XII). Usually the intermediate indoline (X) is not isolated but either (i) hydrolyzed with concomitant formation of the indole ring directly to a compound of formula (I) under standard conditions known to those skilled in the art, or (ii) transformed to a compound of formula (XII) by using a suitable base, for example, an alkali or alkaline earth metal carbonate such as sodium carbonate, potassium carbonate or cesium carbonate, or an organic base such as 1,8-diazabicyclo[5.4.0]undec-7-ene(DBU), 1,5-diazabicyclo[4.3.0]non-5-ene (DBN), 1,4-diazabicyclo[2.2.2]octane (DABCO), pyridine, pyrrolidine, triethylamine, diethylisopropylamine, or Hunig's base, or the like, or a suitable oxidant such as cerium(IV) ammonium nitrate (CAN), manganese(IV) oxide, manganese(III) triacetate, copper(II) acetate/air, chloranil, 2,3-dichloro-5,6-dicyano-1,4-benzoquinone (DDQ), N-methylmorpholine N-oxide, or the like (for example, see H. Dumoulin et al; J. Heterocycl. Chem., 32, 1703, 1995; H. Rapoport et al; Tetrahedron Lett., 5053, 1991; P. Martin et al; Helv. Chim. Acta, 77, 111, 1994; Y. Kikugawa et al, J. Chem. Soc. Perkins Trans 1, 7, 1401, 1984; A. Goti et al; Tetrahedron Lett., 6567, 1996; L. S. Liebeskind et al; J. Org. Chem, 61, 2594, 1996). Preferred reaction inert solvents include, but are not limited to, acetone, methyl ethyl ketone, acetonitrile, dioxane or tetrahydrofuran. Reaction temperatures are preferably in the range of 0° C. to reflux temperature of the solvent, usually in the range of 15° C. to 60° C., but if necessary, lower or higher temperature can be employed. Reaction time is in general from 1 minute to a day, preferably from 30 minutes to 8 hours, however shorter or longer reaction times, if necessary, can be employed. A compound of formula (XII) may be readily hydrolyzed to a compound of formula (I) under standard conditions.

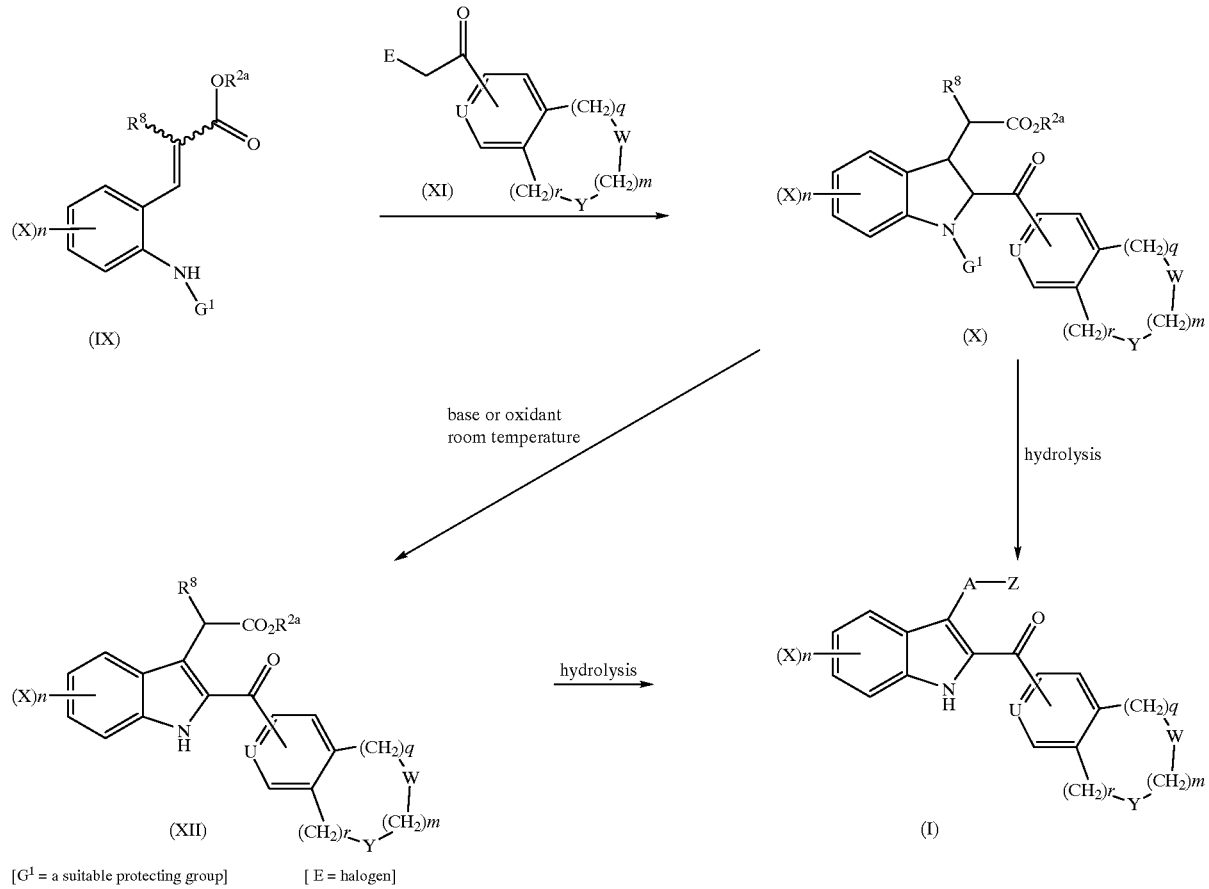

Scheme 3

[$G^1$ = a suitable protecting group]    [E = halogen]

In another embodiment, a compound of formula (I), wherein A is —($R^8$)CH—, Z is $CO_2H$, and $R^8$ is hydrogen or $C_{l-5}$ alkyl may be prepared as illustrated in Scheme 4. For example, treatment of a compound of formula (XIII), wherein $R^8$, $R^{2a}$, X and n are as defined as herein before, with a trialkyltin hydride, e.g., tributyltin hydride usually in the presence of a radical initiator such as, AIBN, affords the intermediate 2-stannylindole (XIV) via an intramolecular radical cyclization as described in J. Am. Chem. Soc., 116, 3127, (1994); T. Fukuyama et al. The intermediate (XIV) generated in situ is subsequently treated with an acyl halide (XV), wherein U and E are as defined herein before, in the presence of a suitable palladium(0) catalyst according to Stille's procedure (for example see. J. K. Stille et al; J. Am. Chem. Soc., 109, 813, 5478, (1987) and J. Am. Chem. Soc., 106, 4833, (1984)) to afford indole (XII) which may be hydrolyzed to a compound of formula (I) by conventional procedure.

Scheme 4

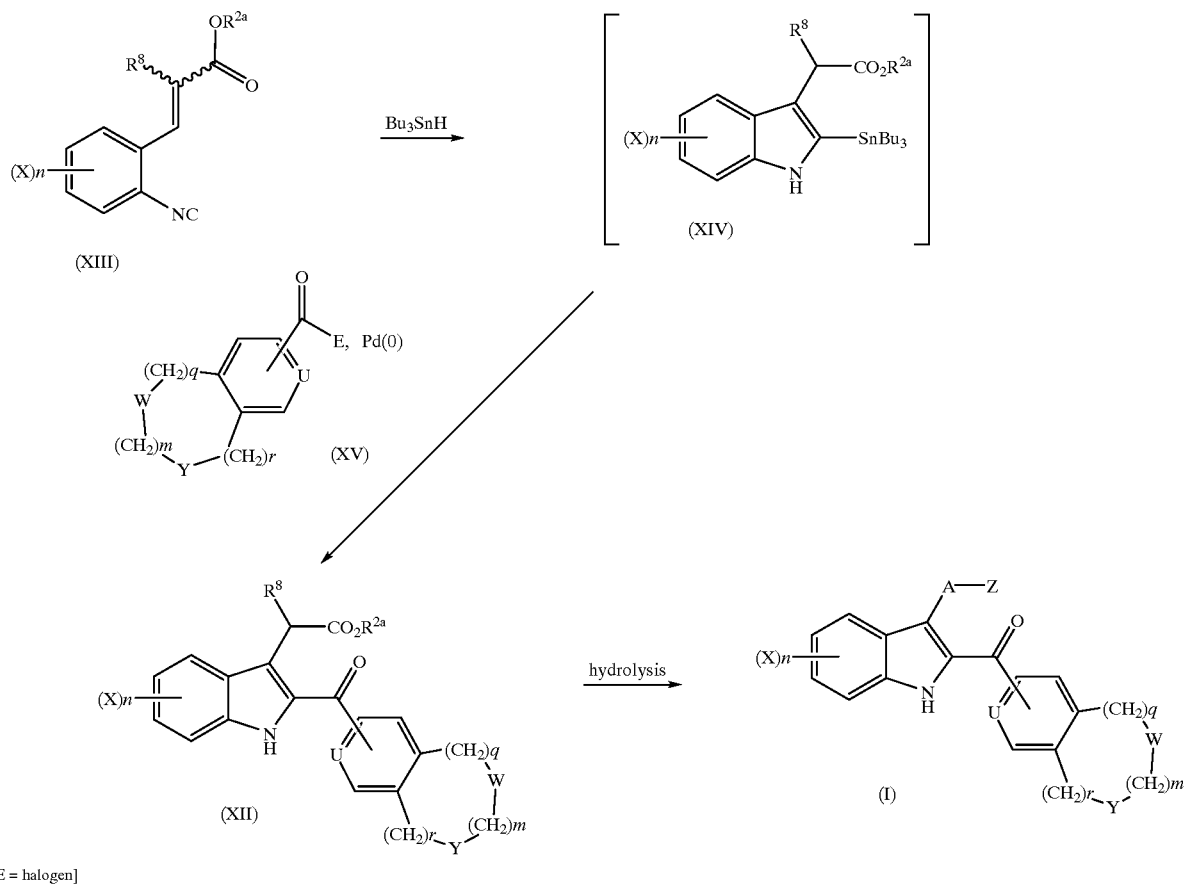

[E = halogen]

Acetic acid compounds of formula (I) as described in the Scheme 4 may be readily transformed to the corresponding ester, a compound of formula (XII), by any conventional method known to those skilled in the art, as depicted in Scheme 5.

Scheme 5

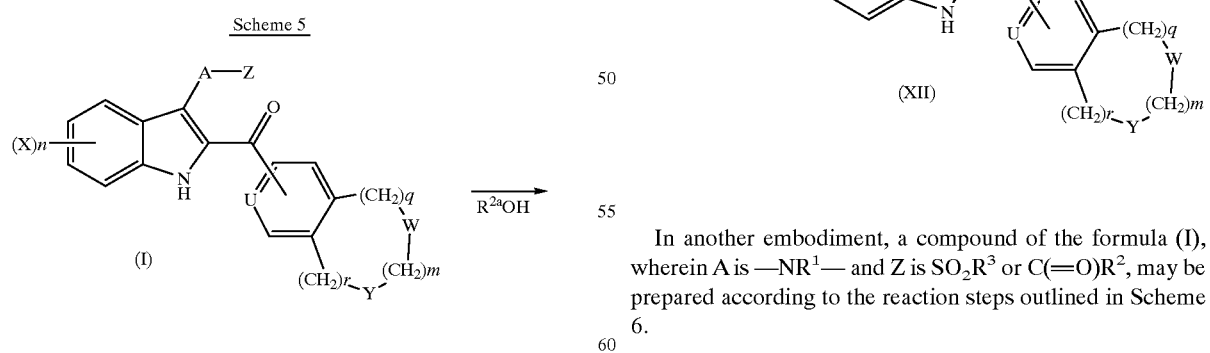

In another embodiment, a compound of the formula (I), wherein A is —$NR^1$— and Z is $SO_2R^3$ or C(=O)$R^2$, may be prepared according to the reaction steps outlined in Scheme 6.

Scheme 6

METHOD A

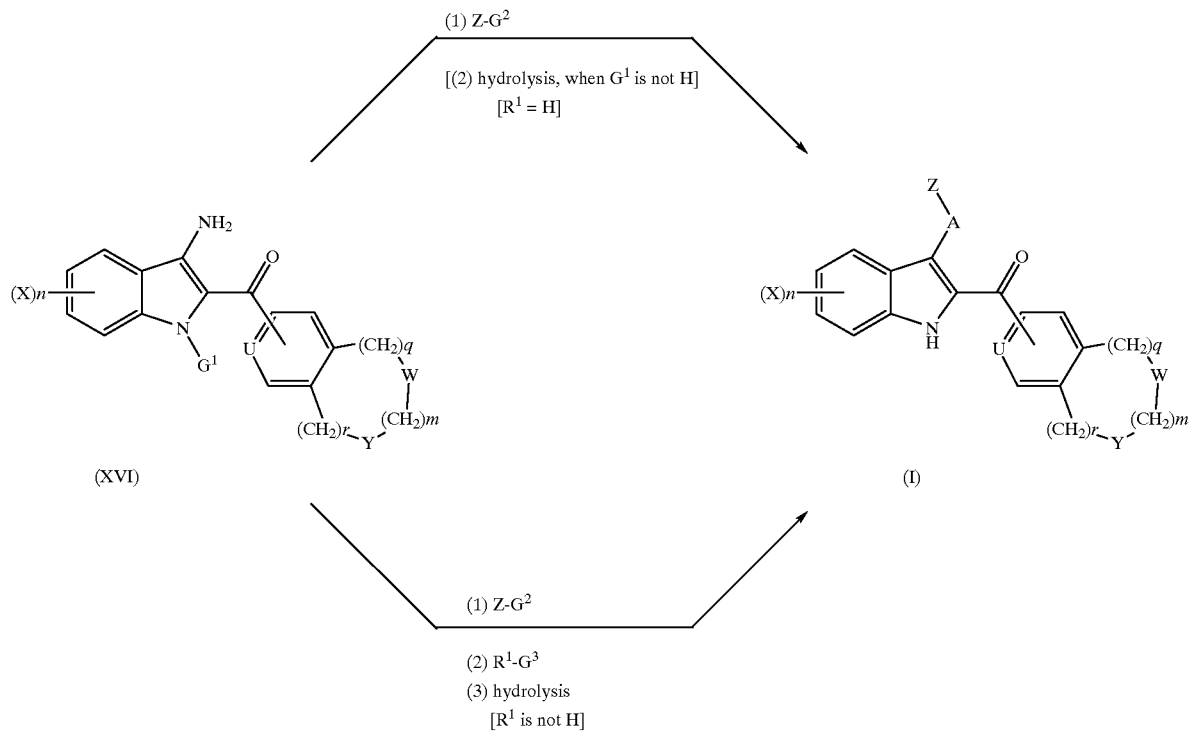

METHOD B

For example, in step 1 of Method A or Method B, a compound of formula (XVI), wherein $G^1$ is hydrogen or a suitable protecting group defined herein before, is reacted with a compound of formula Z—$G^2$ wherein $G^2$ is defined such that the compound of Z—$G^2$ is, for example, a carboxylic acid chloride, a carboxylic acid, a carboxylic acid ester, a carboxylic acid anhydride, a sulfonic acid chloride, a sulfonic acid anhydride or the like. In the instant example, when a compound of formula Z—$G^2$ is, for example, a carboxylic acid chloride, a carboxylic acid anhydride or a sulfonic acid chloride the reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, or the like. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahydrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

Alternatively, when a compound of formula Z—$G^2$ is, for example, a carboxylic acid the intermediate amide obtained from step 1 in either Method A or Method B can be readily prepared by treating the requisite carboxylic acid with a compound of formula (XVI) in the presence of a coupling reagent such as, but not limited to, 1-(dimethylaminopropyl)-3-ethylcarbodiimide (WSC), N,N'-dicyclohexylcarbodiimide (DCC), carbonyldiimidazole, cyanophosphonic acid diethyl ester, or the like. Preferred reaction inert solvents include, but are not limited to, acetone, acetonitrile, dichloromethane, 1,2-dichloroethane, N,N-dimethylformamide, N,N-dimethylacetamide, dimethylsulfoxide, dioxane, tetrahydrofuran or pyridine. Or, for example, under Mitsunobu-type reaction conditions. A suitable condensing reagent in the Mitsunobu reaction is a di-($C_{1-4}$)alkyl azodicarboxylate in the presence of a triarylphosphine, for example, diethyl azodicarboxylate in the presence of triphenylphosphine. Reaction inert solvents of choice include tetrahydrofuran, dichloromethane, dimethylformamide, benzene, toluene, or the like. The reaction temperature is preferably in the range of 0° C. to reflux temperature of the solvent, e.g. 0 to 100° C., but if necessary, temperatures lower or higher can be adopted. Reaction times are, in general, from several minutes to a day, preferably from 20 minutes to 5 hours, however shorter or longer reaction times, if necessary, can be employed.

In step 2 of Method B, the intermediate amide (the group $G^1$ is a suitable protecting group as defined herein above) is reacted with a compound of formula $R^1$—$G^3$ wherein $G^3$ is a selected from a suitable displaceable group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

In step 2 of Method A or step 3 of Method B (the group $G^1$ is a suitable protecting group as defined herein above) the group $G^1$ may be removed by a number of standard procedures known to those skilled in the art (for example, see "Protection of the Amino Group", in *Protective Groups in Organic Synthesis*, 2nd Edition, T. W. Greene and P. G. M. Wuts, Ed., John Wiley and Sons, Inc. 1991, pp. 309–405).

A compound of formula (I), wherein A is —$NR^1$— and Z is $SO_2R^3$ or C(=O)$R^2$, may also be prepared according to the reaction step outlined in Scheme 7. The compound of formula (XVIII) (amide) is used for illustrative purposes only and is not meant to limit the scope of the present invention. Thus, for example, a compound of formula (XVIII) is treated with a compound of formula (XIX) in a reaction inert solvent. In a compound of formula (XIX), M is defined such that compound of formula (XIX) is, for example, the corresponding Grignard or alkali metal reagent, for example, M may be magnesium chloride (MgCl), magnesium bromide (MgBr), or magnesium iodide (MgI), lithium (Li), potassium (K) or sodium (Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (XVIII) is readily accessible by conventional synthetic methods known to those skilled in the art and, of which, are adequately described within the accompanying non-limiting examples.

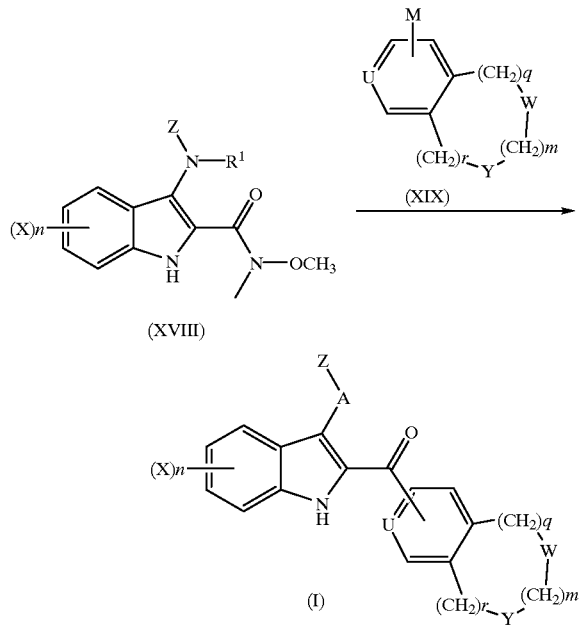

Scheme 7

In another embodiment, compounds of the formula (I), wherein A is —$NR^1$ and Z is C(=O)$NR^4R^5$, are prepared according to the reaction steps outlined in Scheme 8. For example, a compound of formula (XX), wherein $G^1$ is hydrogen or a suitable protecting group as herein before, is reacted with a compound of formula $HNR^4R^5$. The reactants may be heated together in the absence or presence of a reaction inert solvent. Preferred reaction inert solvents include, but are not limited to, benzene, toluene, xylene, o-dichlorobenzene, nitrobenzene, pyridine, 1,2-dichloroethane, dichloromethane, acetonitrile, dioxane, N,N-dimethylformamide, or the like. If necessary, the reaction conducted in the presence of base. A preferred base is selected from, for example, but not limited to, an alkali or alkaline earth metal hydroxide or carbonate such as sodium hydroxide, potassium hydroxide, sodium carbonate, potassium carbonate, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahydrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group $G^1$ is a suitable protecting group as defined herein above, if necessary, the group $G^1$ may be removed by a number of standard procedures known to those skilled in the art (for example, see "Protection of the Amino Group", in *Protective Groups in Organic Synthesis*, 2nd Edition, T. W. Greene and P. G. M. Wuts, Ed., John Wiley and Sons, Inc. 1991, pp. 309–405).

Scheme 8

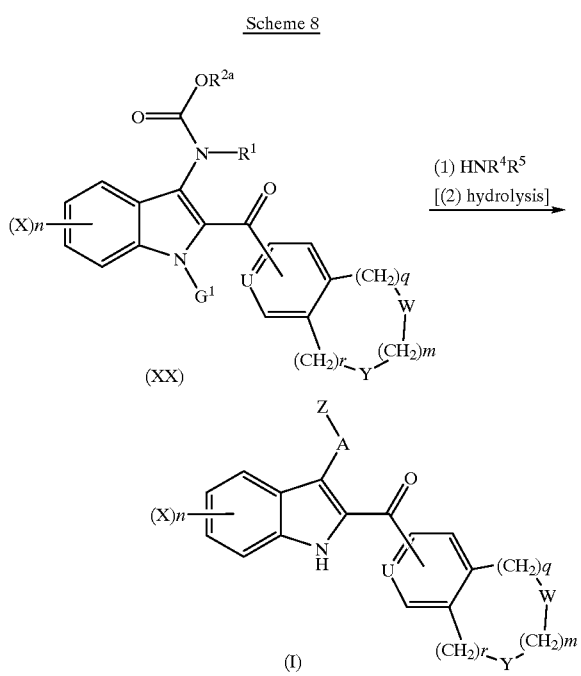

In another embodiment, compounds of the formula (I), wherein A is NH and Z is C(=O)NH$_2$, and compounds of formula (I), wherein A is NH and Z is C(=O)NHR$^4$, are prepared according to the reaction steps outlined in Scheme 9. For example, a compound of formula (XVI), wherein G$^1$ is hydrogen or a suitable protecting group as herein before, is reacted with a compound of formula M—OCN, or a compound of formula R$^4$NCO. In a compound of formula M-OCN, M is defined such that compound of formula M-OCN is, for example, the corresponding alkali or alkaline earth metal reagent, for example, M may be sodium, potassium.

The reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, dichloromethane, or the like. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed.

When the group G$^1$ is a suitable protecting group as defined herein above, the group G$^1$ may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

Scheme 9

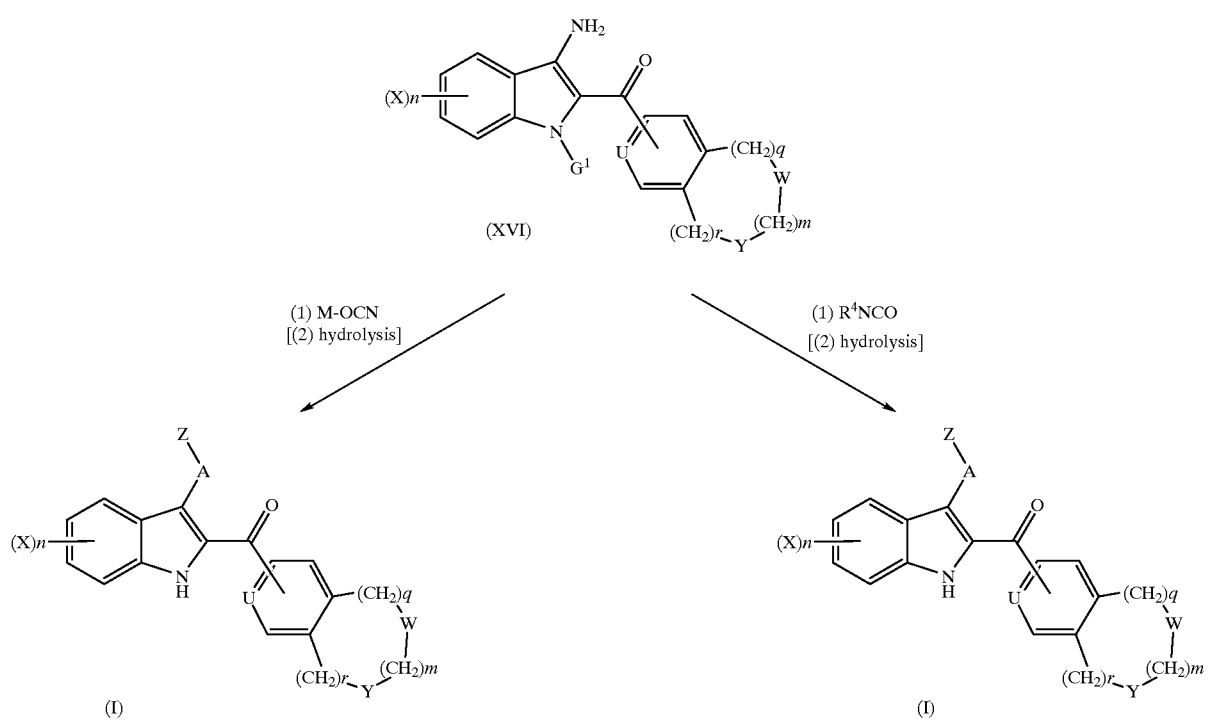

A compound of formula (XVI) may be prepared by a number of synthetic procedures known to those skilled in the art. The following representative examples as described hereinafter are illustrative and are not meant to limit the scope of the invention in anyway.

For example, a compound of formula (XVI) is readily accessible from the appropriate 2-aminobenzonitrile (XXIV), wherein $G^1$ is a suitable protecting group as herein before, as illustrated in Scheme 10 (For example, see E. E. Garcia, L. E. Benjamin and R. Ian Fryer, *J. Heterocycl Chem.*, 10, 51(1973)). Thus, the requisite 2-aminobenzonitrile (XXIV) is reacted with a compound of formula (XI), wherein E is halogen, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, sodium hydride or potassium hydride. Preferred reaction inert solvents include, but are not limited to, acetonitrile, N,N-dimethylformamide, N,N-dimethylacetamide, dimethylsulfoxide, dioxane or tetrahydrofuran. Reaction temperatures are preferably in the range of −40 to 250° C., usually in the range of 0° C. to reflux temperature of solvent, but if necessary, lower or higher temperature can be employed. Reaction time is in general from 1 minute to a day, preferably from 30 minutes to 5 hours, however shorter or longer reaction times, if necessary, can be employed.

Scheme 10

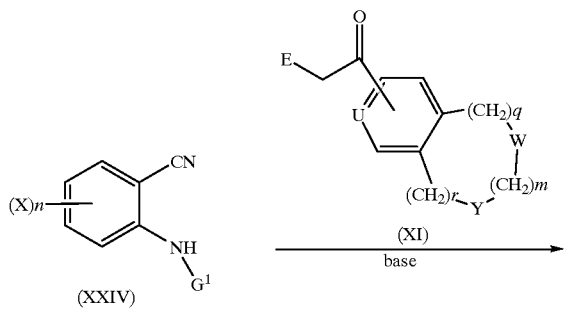

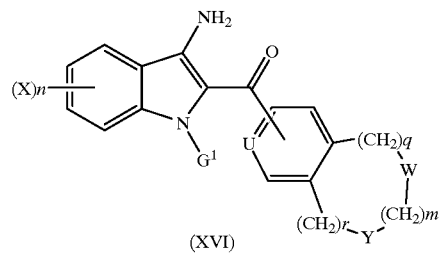

Alternatively, a compound of formula (XVI), wherein $G^1$ is hydrogen, may be prepared according to the reaction steps depicted in Scheme 11. For example, the compound of formula (XVI) may be prepared from the requisite nitro compound of formula (XXVI) by reduction in the presence of suitable reducing agent by conventional methods known to those skilled in the art. For example, tin (II) chloride in ethanol (F. D. Bellamy and K. Ou, *Tetrahedron Lett.*, 25, 839 (1984)), iron—ammonium chloride in aqueous ethanol (K. Ramadas and N. Srinivasan, *Synth. Commun.*, 22, 3189 (1992)), or zinc dust or iron in acetic acid (E. Wertheim, *Org. Synth. Coll. Vol.* 2., 160 (1943)), or by catalytic hydrogenolysis. Preferred catalysts are, for example, palladium-on-charcoal or Raney-Nickel (C. F. H. Allen and J. Vanallan, *Org. Synth. Coll.* Vol 3., 63 (1955)). The nitro compound of formula (XXVI) is readily accessible by conventional synthetic methods known to those skilled in the art and, of which, are adequately described within the accompanying non-limiting examples.

Scheme 11

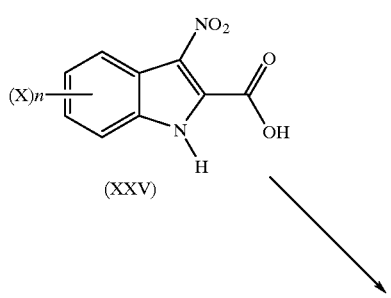

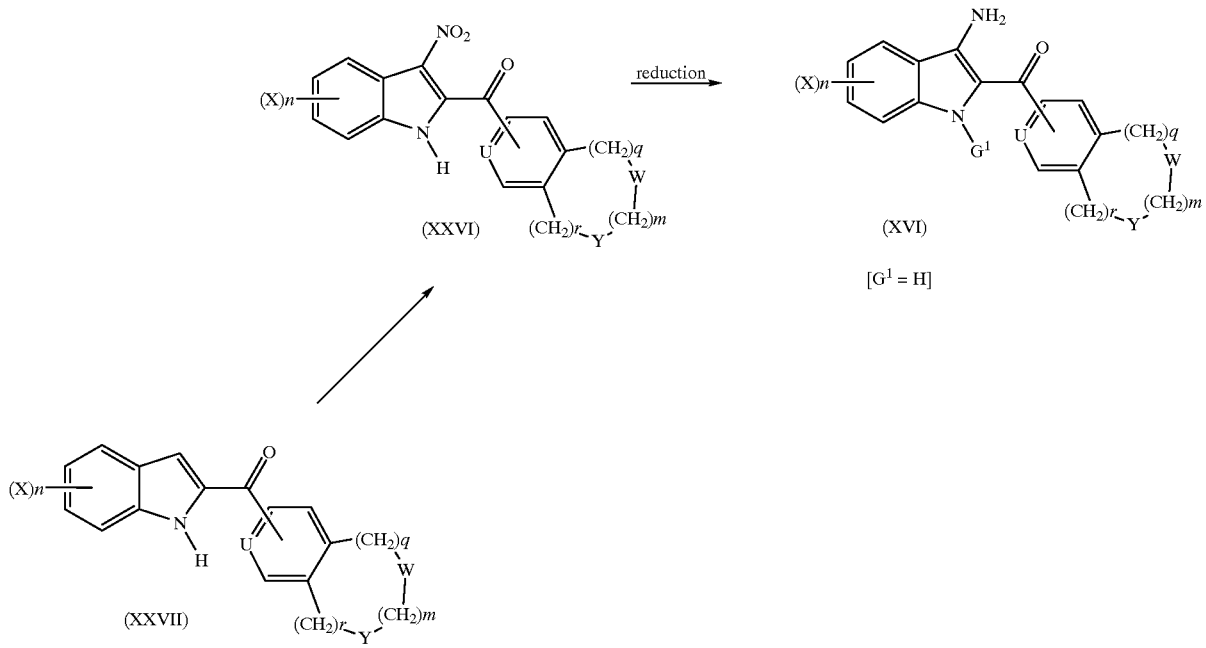

The starting materials III, IX, XI, XIII, XV, XVI, XVIII, XIX, XX, XXIV, XXV, XXVII in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds of the present invention are capable of forming addition salts with inorganic or organic acids. The pharmaceutically acceptable acid salts of the compounds of formula (I) are those which form non-toxic addition salts, such as, the hydrochloride, hydrobromide, sulfate or bisulfate, acetate, benzoate, besylate, citrate, fumarate, glucuronate, hippurate, lactate, tartrate, saccharate, succinate, maleate, methanesulfonate, p-toluenesulfonate, phosphate and pamoate (i.e., 4,4'-methylene-bis(3-hydroxy-2-naphthoate)) salts. The pharmaceutically acceptable acid salts may be prepared by conventional techniques.

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

An example of prodrug of the compound of formula (I) is a compound of the formula (I), wherein the 1st position of indole ring is substituted with a group selected from hydroxymethyl, —C(O)—$C_{1-4}$ alkyl, —C(O)—(NH$_2$)CH—($C_{1-4}$ alkyl), —C(O)—phenyl, —CH$_2$NHC(O)-aryl, —CH$_2$—$C_{1-4}$alkyl-O—C(O)—$C_{1-4}$alkyl, —$C_{1-4}$ alkyl—pyridyl, —C(O)CH$_2$NR$_2$ and —CH$_2$N($C_{1-4}$ alkyl)$_2$.

Another example of prodrug of the compound of formula (I) is a compound of the formula (I), wherein the carboxyl group is substituted with a group selected from $C_{1-4}$ alkyl, —CH$_2$—$C_{1-4}$alkyl-O—C(O)—$C_{1-4}$alkyl, —CH$_2$—$C_{1-4}$alkyl-O—C(O)—N($C_{1-4}$alkyl)$_2$, —CH$_2$C(O)—N($C_{1-4}$ alkyl)$_2$, —CH$_2$—$C_{1-4}$alkyl-O—C(O)-O—$C_{1-4}$ alkyl, ethyl-OH and —CH$_2$CO$_2$H.

The compounds of the formula (I) of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.01 mg to 10 mg per kg of body weight per day, single or divided dosage is most desirably employed in humans for the treatment of abovementioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

Combination with Other Drugs

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthma, bronchitis, inmenstrual cramps, tendinitis, bursitis, and skin related conditions such as psoriasis, eczema, burns and dermatitis. Combinations of the invention also would be useful to treat gastrointestinal conditions such as inflammatory bowel disease. Crohn's disease, gastritis, irritable bowel syndrome and ulcerative colitis and for the prevention of colorectal cancer. Combinations of the invention would be useful in creating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclercsis, sarcoidosis, nephrotic syndrome, Behcet's syndrome, polymyositis, gingivitis, hypersensitivity, Conjunctivitis, swelling occurring after injury, myocardial ischemia, and the like. The combinations would also be useful for the treatment of certain central nervous system disorders such as Alzheimer's disease and dementia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Compounds of formula (I) will be useful as a partial or complete substitute for conventional NSAID's in preparations wherein they are presently co-administered with other agents or ingredients. Thus, the invention encompasses pharmaceutical compositions for treating COX-2 mediated diseases as defined above comprising a non-toxic therapeutically effective amount of the compound of formula (I) and one or more ingredients such as another pain reliever including acetaminophen or phenacetin; a potentiator including caffeine; an $H_2$-antagonist, aluminum or magnesium hydroxide, simethicone, a decongestant including phenylephrine, phenylproanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprotol or rosaprostol; a diuretic; a sedating or non-sedating antihistamine; anticancer agents such as angiostatin and endostatin; anti-Alzheimers such as Doepezil and Tacrine hydrochloride; and TNF alpha inhibitors such as Etanercept.

These cyclooxygenase inhibitors can further be used in combination with a nitric oxide inhibitors disclosed in WO 96/28145.

Also, the invention encompasses pharmaceutical compositions for treating COX-2 mediated diseases as defined above comprising a non-toxic therapeutically effective amount of the compound of formula (I) and one or more anti-ulcer agent and/or prostaglandins, which are disclosed in WO 97/11701.

The useful prostaglandins include misoprostol, plus-minus methyl 11α,16-dihydroxy-16-methyl-9-oxoprost 13E-en-1-oate; enisoprost and methyl-7-[2B-[6-(1-cyclopenten-1-yl)-4-hydroxy-4-methyl-1 E, 5E-hexadienyl]-3α-hydroxy-5-oxo 1R, 1α-cyclopentyl]-4Z-heptenoate. Prostaglandins within the scope of the invention also include arbaprostil, enprostil, rioprostol, nocloprost, mexiprostil, ornoprostol, dimoxaprost, tiprostanide and rosaprostol.

The present compounds may also be used in co-therapies, partially or completely, in place of other conventional antiinflammatories, such as together with steroids, 5-lipoxygenase inhibitors, $LTB_4$ antagonists and $LTA_4$ hydrolase inhibitor's.

An example of $LTB_4$ is disclosed in WO97/29774. Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, Ono compound ONO-LB457, Searle compound SC-S3228, calcitrol, Lilly compounds LY-210073, LY223982, LY233469, and LY255283, Ono compound ONO-LB-448, Searle compounds SC-41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-61S, Lilly compound LY-293111, Ono compound ONO-4057 and Terumo compound TMK-688.

An example of 5-LO inhibitors is disclosed in WO97/29776. Suitable 5-LO inhibitors include, among others, masoprocol, tenidap, zileuton, pranlukast, tepoxalin, rilopirox, flezelastine hydrochloride, enazadrem phosphate and bunaprolast.

An example of $LTA_4$ hydrolase inhibitors is disclosed in WO97/29774. Suitable $LTA_4$ hydrolase inhibitors include, among others, Rhone-Poulenc Rorer RP-64966.

The administration of the present invention may be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche R0-32-3555, or alpha,beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co EX-015, fazarabine, floxuridine, fludarabine phosphate, 5-fluorouracil, N-(2'-furanidyl)-5-fluorouracil, Daiichi Seiyaku F0-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, Iomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067. Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-Ol, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile. amsacrine, Angiostat, ankinomycin, anti-neoplaston AIO, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-lO, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-1OO, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross H0-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MECT Corp KI-8110, American Cyanamid L-623, leukoregulin, Ionidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-lOOl, ICRT peptide D, piroxantrone, polyhaematoporphyrin, polypreic acid, Efamol porphyrin, probimane, procarbazine, proglurnide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1-102, MN-159, N-acylated-dehydroalanines, TGF-Genentech, tiprotimod, amifostine, WR-151327, FUT-187, ketoprofen transdermal, naburnetone, superoxide dismutase (Chiron) and superoxide disrrtutase Enzon.

Methods for preparation of the antineoplastic agents described above may be found in the literature. Methods for preparation of doxorubicin, for example, are described in U.S. Pat. No. 3,590,028 and No. 4,012,448. Methods for preparing metallomatrix protease inhibitors are described in EP 780386, WO97/20824. WO96/15096. Methods for preparing SOD mimics are described in EP 524,101. Methods for preparing alpha, beta, inhibitors are described in WO97/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibuprofen, salicylic acid derivatives such as aspirin, diclofenac, ketorolac, piroxicam, meloxicam, mefenamic acid, sulindac, tolmetin sodium, zomepirac, fenoprofen, phenylbutazone, oxyphenbutazone, nimesulide, zaltoprofen and letodolac.

Method for Assessing Biological Activities

The activity of the compounds of the formula (I) of the present invention was demonstrated by the following assays.
In Vitro Assays
Human Cell Based COX-1 Assay Human peripheral blood obtained from healthy volunteers was diluted to $\frac{1}{10}$ volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 μl aliquots, final $2.0 \times 10^7$ cells/ml) was placed in a 96-well U bottom plate and 10 μl aliquots of 12.6 mM $CaCl_2$ added. Platelets were incubated with A23187 (final 10 μM, Sigma) with test compound (0.1–100 μM) dissolved in DMSO (final concentration; less than 0.01%) at 37° C. for 15 min. The reaction was stopped by addition of EDTA (final 7.7 mM) and $TxB_2$ in the supernatant quantitated by using a radioimmunoassay kit (Amersham) according to the manufacturer's procedure.
Human Cell based COX-2 assay The human sell based COX-2 assay is carried as previously reported by Moore et al., Inflam. Res., Vol. 45, pp. 54- , 1996. Confluent human umbilical vein endothelial cells (HUVECs, Morinaga) in a 96-well U bottom plate are washed with 100 μl of RPMI1640 containing 2% FCS and incubation with hIL-1β(final concentration 300 U/ml, R & D Systems) at 37° C. for 24 hours. After washing, the activated HUVECs are stimulated with A23187 (final concentration 30 μM) in Hanks buffer containing 0.2% BSA, 20 mM Hepes and a test compound (0.1 nM–100 μM) dissolved in DMSSO (final concentration; less than 0.01%) 37° C. for 15 minutes. 6-Keto-$PGF_{1\alpha}$, stable metabolite of $PGI_2$, in the supernatant is quantitated after adequate dilution by using a radioimmunoassay kit (supplied by Amersham) according to the manufacture's procedures.
Canine In Vitro Assays The following canine cell based COX 1 and COX-2 assays have been reported in Ricketts et al., Evaluation of Selective Inhibition of Canine Cyclooxygenase 1 and 2 by Carprofen and Other Nonsteroidal Anti-inflammatory Drugs, American Journal of Veterinary Research, 59 (11), 1441–1446.

Protocol for Evaluation of Canine COX-1 Activity

Test dug compounds were solubilized and diluted the day before the assay was to be conducted with 0.1 mL of DMSO/9.9 mL of Hank's balanced salts solution (BBSS), and stored overnight at 40° C. On the day that the assay was carried out, citrated blood was drawn from a donor dog, centrifuged at 190×g for 25 min at room temperature, and the resulting platelet-rich plasma was then transferred to a new tube for further procedures. The platelets were washed by centrifuging at 1500×g for 10 min at room temperature. The platelets were washed with platelet buffer comprising Hank's buffer (Ca free) with 0.2% bovine serum albumin (BSA) and 20 mM HEPES. The platelet samples were then adjusted to $1.5 \times 10^7$/mL, after which 50 µl of calcium ionophore (A23187) together with a calcium chloride solution were added to 50 µl of test drug compound dilution in plates to produce final concentrations of 1.7 µM A23187 and 1.26 mM Ca. Then, 100 µl of canine washed platelets were added and the samples were incubated at 37° C. for 15 min, after which the reaction was stopped by adding 20 µl of 77 mM EDTA. The plates were then centrifuged at 2000×g for 10 min at 4° C., after which 50 µl of supernatant was assayed for thromboxane $B_2$ ($TXB_2$) by enzyme-immunoassay (EIA). The pg/mL of $TXB_2$ was calculated from the standard line included on each plate, from which it was possible to calculate the percent inhibition of COX-1 and the $IC_{50}$ values for the test drug compounds.

Protocol for Evaluation of Canine COX-2 Activity

A canine histocytoma (macrophage-like) cell line from the American Type Culture Collection designated as DH82, was used in setting up the protocol for evaluating the COX-2 inhibition activity of various test drug compounds. There was added to flasks of these cells 10 µg/mL of LPS, after which the flask cultures were incubated overnight. The same test drug compound dilutions as described above for the COX-1 protocol were used for the COX-2 assay and were prepared the day before the assay was carried out. The cells were harvested from the culture flasks by scraping, and were then washed with minimal Eagle's media (MEM) combined with 1% fetal bovine serum, centrifuged at 1500 rpm for 2 min, and adjusted to a concentration of $3.2 \times 10^5$ cells/mL. To 50 µl of test drug dilution there was added 50 µl of arachidonic acid in MEM to give a 10 µM final concentration, and there was added as well 100 µl of cell suspension to give a final concentration of $1.6 \times 10^5$ cells/mL. The test sample suspensions were incubated for 1 hr and then centrifuged at 1000 rpm for 10 min at 4° C., after which 50 µl aliquots of each test drug sample were delivered to EIA plates. The EIA was performed for prostaglandin $E_2$ ($PGE_2$), and the pg/mL concentration of $PGE_2$ was calculated from the standard line included on each plate. From this data it was possible to calculate the percent inhibition of COX-2 and the $IC_{50}$ values for the test drug compounds. Repeated investigations of COX-1 and COX-2 inhibition were conducted over the course of several months. The results are averaged, and a single COX-1: COX-2 ratio is calculated.

Whole blood assays for COX-1 and COX-2 are known in the art such as the methods described in C. Brideau, et al., A Human Whole Blood Assay for Clinical Evaluation of Biochemical Efficacy of Cyclooxygenase Inhibitors, Inflammation Research, 45, 68–74, (1996). These methods may be applied with feline, canine or human blood as needed.

In Vivo Assays

Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with X-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) was measured and the increase in volume (V3-V0) calculated. Since maximum inhibition attainable with classical NSAIDs is 60–70%, ED30 values were calculated.

Gastric Ulceration in Rats

The gastric ulcerogenicity of test compound was assessed by a modification of the conventional method (Ezer et al., *J. Pharm. Pharmacol.*, 28, 655, 1976; Cashin et al, *J. Pharm. Pharmacol*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Some compounds prepared in the Working Examples as described herein after were tested by these methods, and showed $IC_{50}$ values of 0.001 µM to 10 µM with respect to inhibition of COX-2.

Also, the above-mentioned most preferred compounds were tested by these methods, and showed $IC_{50}$ values of 0.001 µM to 0.5 µM with respect to inhibition of COX-2.

COX-2 selectivity can be determined by ratio in terms of $IC_{50}$ value of COX-1 inhibition to COX-2 inhibition. In general, it can be said that a compound showing a COX-1/COX-2 inhibition ratio of more than 2 has good COX-2 selectivity.

Some compounds prepared in Examples showed COX-1/COX-2 inhibition ratio of more than 10.

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or microanalysis. Yields are given for illustrative purposes only. Flash column chromatography was carried out using Merck silica gel 60 (230–400 mesh ASTM). Low-resolution mass spectral data (ES) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

Example 1

Methyl [6—chloro-2-[(5,6,7,8-tetrahydroisoquinolin-3yl)carbonyl]-1H-indol-3-yl] acetate Step 1. Methyl trans -4-chloro-2-[(phenylsulfonyl)amino] cinnamate To a solution of methyl trans-4-chloro-2-aminocinnamate (R. W. Carling et al., *J.Med.Chem.*, 1993, 36, 3397., 30.7 g, 0.15 mol) and pyridine (36 ml, 0.45 mol) in dichloromethane (500 ml) was added benzenesulfonyl chloride (20 ml, 0.16 mol). After stirring for 20 h, methanol (50 ml) was added and the mixture was concentrated. The residual solids were dissolved in dichloromethane (700 ml) and washed with 2N aqueous HCl (150 ml), brine (150 ml) and dried ($MgSO_4$). After removal of solvent, the residual solids were recrystallized from ethanol to give 40 g (76%) of the title compound as pale yellow solids.

$^1$H-NMR ($CDCl_3$) δ: 7.77–7.71 (2H, m), 7.59–7.52 (1H, m), 7.48–7.35 (5H, m), 7.20 (1H, dd, J=2.0, 8.4 Hz), 6.85 (1H, br s), 6.15 (1H, d, J=15.8 Hz), 3.78 (3H, s).

Step 2. Methyl [6-chloro-2-[(5,6,7,8-tetrahydroisoquinolin-3-yl)carbonyl]-1H-indol-3-yl]acetate A mixture of 3-bromoacetyl-5,6,7,8-tetrahydroisoquinoline* (524.9 mg), methyl trans-4-chloro-2-[(phenylsulfonyl)amino]cinnamate (step 1, 351.8 mg, 1.0 mmol) and potassium carbonate (690 mg, 5.0 mmol) in acetone was stirred at room temperature for 16 h. To the resulting mixture was added 1,8-diazabicyclo[5.4.0]undec-7-ene (DBU) (0.3 ml, 2.0 mmol) and the resulting mixture was stirred for an additional 8 h. The reaction mixture was concentrated and the residue was partitioned between ethyl acetate (40 ml) and water (40 ml). The aqueous layer was separated and extracted with ethyl acetate (40 ml×3). The combined organic layers were dried ($MgSO_4$), and concentrated. Purification by flash column chromatography eluting with hexane/ethyl acetate (3/1) afforded 41.7 mg (10.9%) of the title compound as pale yellow crystalline solids.

$^1$H-NMR ($CDCl_3$) δ: 12.6 (1H, br s), 8.43 (1H, s), 8.04 (1H, s), 7.60–7.14 (3H, m), 4.31 (2H, s), 3.72 (3H, s), 2.95–2.80 (4H, m), 1.94–1.78 (4H,m).

*3-bromoacetyl-5,6,7,8-tetrahydroisoquinoline was prepared as follows:

3-Acetyl-5,6,7,8-tetrahydroisoquinoline;

A mixture of 5,6,7,8-tetrahydroisoquinoline (3.9 ml, 30.0 mmol), silver nitrate (407.7 mg, 2.4 mmol), ammonium persulfate (10.27 g, 45.0 mmol), and sulfuric acid (1.6 ml, 30.0 mmol) in water (300 ml)-dichloromethane (300 ml) was stirred at 40° C. for 5 h. After cooling to room temperature, the mixture was made basic with 2N aqueous NaOH and the organic layer was separated. The aqueous layer was extracted with dichloromethane (300 ml). The combined organic layers were dried ($MgSO_4$) and concentrated. The residue was purified by flash column chromatography eluting with hexane/ethyl acetate (3/1) to afford 287.7 mg (5.5%) of the title compound as an brown oil.

$^1$H-NMR ($CDCl_3$) δ: 8.35 (1H, s), 7.75 (1H, s), 2.84–2.79 (4H, m), 2.69 (3H, s), 1.89–1.79 (4H, m).

3-Bromoacetyl-5,6,7,8-tetrahydroisoquinoline;

To a mixture of 3-acetyl-5,6,7,8-tetrahydroisoquinoline (287.7 mg, 1.64 mmol) and hydrobromic acid (25% solution in acetic acid, 3.1 ml) was added a solution of bromine (93.3 μl, 1.81 mmol) in acetic acid (0.4 ml) at 0° C. The mixture was stirred at room temperature for an additional 3 h. and concentrated. The residue was made basic with saturated aqueous hydrogen bicarbonate and extracted with diethyl ether (150 ml). The organic layer dried ($MgSO_4$) and concentrated to afford 524.9 mg of the crude title compound as an brown oil.

$^1$H-NMR ($CDCl_3$) δ: 8.35 (1H, s), 7.88 (1H, s), 4.87 (2H, s), 2.9–2.8 (4H, m), 1.9–1.82 (4H, m).

Example 2

[6—chloro-2-[(5,6,7,8-tetrahydroisoquinolin-3-yl) carbonyl]-1H-indol-3-yl]acetic acid To a mixture of methyl [6-chloro-2-[(5,6,7,8-tetrahydroisoquinolin-3-yl)carbonyl]-1H-indol-3-yl]acetate (Example 1) in MeOH (20 ml)-THF (20 ml) was added 2N aqueous NaOH (0.6 ml, 1.2 mmol) at room temperature and the resulting mixture was heated at reflux temperature for 8 h. The mixture was cooled and concentrated. The residue was dissolved in water (20 ml) and washed with diethyl ether (20 ml×3). The aqueous layer was acidified with 2N aqueous HCl and extracted with ethyl acetate (40 ml×3). The combined organic layers were dried ($MgSO_4$) and concentrated. The residue was recrystallized from ethyl acetate to afford 23.3 mg (60.7%) of the title compound as yellow solids.

m.p.: 225° C.

IR (KBr): 3422, 1699, 1645, 1537, 1319, 1200, 1061, 991 $cm^{-1}$.

$^1$H-NMR (DMSO-$d_6$) δ: 12.30 (1H, br s), 8.52 (1H, s), 7.84 (1H, s), 7.78 (1H, d, 8.75 Hz), 7.74–7.09 (2H, m), 4.08 (2H, s), 2.90–2.83 (4H, m), 1.85–1.77 (4H, m).

MS (EI) m/z: 368 ($M^+$).

Example 3

Methyl [6-chloro-2-[(2,3-dihydro-1,4-benzodioxin-6-yl)carbonyl]-1H-indol-3-yl]acetate The title compound was prepared according to the procedure described in step 2 of Example 1 from 6-bromoacetyl-2,3-dihydro-1,4-benzodioxine (*J. Med. Chem.* 1972, 15, 49) and methyl trans-4-chloro-2-[(phenylsulfonyl)amino]cinnamate (Example 1, step 1).

$^1$H-NMR ($CDCl_3$) δ: 8.85 (1H, br s), 7.56 (1H, d, 8.56 Hz), 7.41–7.33 (4H, m), 7.15 (1H, dd, 8.56 Hz, 1.81 Hz), 6.98–6.94 (1H, m), 4.38–4.29 (4H, m), 3.88 (2H, s), 3.68 (3H, s).

Example 4

[6—Chloro-2-[(2,3-dihydro-1,4-benzodioxin-6-YL) carbonyl]-1H-indol-3-yl]acetic acid The title compound was prepared according to the procedure described in Example 2 from methyl [6-chloro-2-[(2, 3-dihydro-1,4-benzodioxin-6-yl)carbonyl]-1H-indol-3-yl] acetate (Example 3).

m.p.: 233° C.

IR (KBr): 3321, 1707, 1612, 1568, 1429, 1317, 1288, 1263, 1225, 1119, 1065, 1005, 922, 895 cm$^{-1}$.

$^1$H-NMR (DMSO-d$_6$) δ: 11.73 (1H, brs), 7.70 (1H, d, 8.72 Hz), 7.47 (1H, d, 1.65 Hz), 7.33–7.25(2H, m), 7.14–7.02 (2H, m), 4.37–4.31 (4H, m), 3.82 (2H, s).

Example 5

Methyl [2-[(2,3-dihydro-1,4-benzodioxin-6-yl) carbonyl]-5-trifluoromethyl-1H-indol-3-yl]acetate Step 1. Methyl trans-2-amino-5-(trifluoromethyl)cinnamate A mixture of 4-amino-3-bromobenzotrifluoride (2.0 g, 8.33 mmol), methyl acrylate (1.9 ml, 20.83 mmol), palladium acetate (224 mg, 1.00 mmol), tri-o-tolylphosphine (1.2 g, 4.00 mmol), triethylamine (4.5 ml) in acetonitrile (17 ml) were stirred at reflux temperature. After 2 h, methyl acrylate (1.0 ml, 10.41 mmol), palladium acetate (112 mg, 0.5 mmol), tri-o-tolylphosphine (0.6 g, 2.00 mmol) and triethylamine (2.3 ml) were added, and the mixture was stirred at reflux temperature for an additional 5 h. The mixture was concentrated and the residue was diluted in ethyl acetate. After washing with water the organic layer was dried (MgSO$_4$), and concentrated. Purification by flash column chromatography eluting with hexane/ethyl acetate (gradient elution from 5:1 to 3:1) to afford 1.65 g (80.8%) of the title compound as yellow crystals.

$^1$H-NMR (CDCl$_3$) δ: 7.77 (1H, d, J=15.8 Hz), 7.61 (1H, s), 7.39 (1H, d, J=8.4 Hz), 6.74 (1H, d, J=8.4 Hz), 6.41 (1H, dd, J=15.8, 1.5 Hz), 4.29 (2H, m), 3.82 (3H, m).

Step 2. Methyl trans-2-(phenylsulfonyl)amino-5-(trifluoromethyl)cinnamate

The title compound was prepared according to the procedure described in step 1 of Example 1 from methyl trans-2-amino-5-(trifluoromethyl)cinnamate (step 1).

$^1$H-NMR (CDCl$_3$) δ: 7.79–7.76 (2H, m), 7.66 (1H, m), 7.60–7.44 (6H, m), 7.06 (1H, br s), 6.26 (1H, d, J=15.8 Hz), 3.81 (3H, s).

Step 3. Methyl [2-[(2,3-dihydro-1,4-benzodioxin-6-yl)carbonyl]-5-trifluoromethyl-1H-indol-3-yl]acetate The title compound was prepared according to the procedure described in step 2 of Example 1 from 6-bromoacetyl-2,3-dihydro-1,4-benzodioxin (*J.Med. Chem.*, 1972, 15, 49) and methyl trans-2-(phenylsulfonyl)amino-5-(trifluoromethyl)cinnamate (step 2).

$^1$H-NMR (CDCl$_3$) δ: 9.19 (1H, br s), 7.95 (1H, m), 7.58–7.47 (2H, m), 7.38–7.35 (2H, m), 6.98–6.95 (1H, m), 4.37–4.29 (4H, m), 3.91 (2H, s), 3.70 (3H, s).

Example 6

[2-[(2,3-dihydro-1,4-benzodioxin-6-yl)carbonyl]-5-trifluoromethyl-1H-indol-3-yl]acetic acid The title compound was prepared according to the procedure described in Example 2 from methyl [2-[(2,3-dihydro-1,4-benzodioxin-6-yl)carbonyl]-5-trifluoromethyl-1H-indol-3-yl]acetate (Example 5).

m.p.: >250° C.

IR (KBr): 3304, 1701, 1624, 1578, 1508, 1333, 1288, 1236, 1165, 1109, 1049, 1011, 893, 820 cm$^{-1}$.

$^1$H-NMR (DMSO-d$_6$) δ: 12.05 (1H, br s), 8.12 (1H, s), 7.66–7.54 (2H, m), 7.35–7.27 (2H, m), 7.05 (1H, d, 8.40 Hz), 4.37–4.31 (4H, m), 3.90 (2H, s).

Example 7

Methyl [6—chloro-2-[(2,3-dihydro-1-benzofuran-5-yl)carbonyl]1H-indol-3-yl]acetate The title compound was prepared according to the procedure described in step 2 of Example 1 from 5-bromoacetyl-2,3-dihydro-1-benzofuran* and methyl trans-4-chloro-2-[(Phenylsulfonyl)amino]cinnamate (Example 1, step 1).

$^1$H-NMR (CDCl$_3$) δ: 9.03 (1H, br s), 7.73–7.64 (2H, m), 7.55 (1H, d, 8.72 Hz), 7.39 (1H, d, 1.66 Hz), 7.15–6.82 (2H, m), 4.69 (2H, t, 8.72 Hz), 3.85 (2H, s), 3.67 (3H, s), 3.26 (2H, t, 8.72 Hz).

*5-Bromoacetyl-2,3-dihydro-1-benzofuran was prepared from 5-acetyl-2,3-dihydro-1-benzofuran according to the procedure for preparing 3-bromoacetyl-5,6,7,8-tetrahydroisoquinoline described in Example 1.

$^1$H-NMR (CDCl$_3$) δ: 7.98–6.81 (3H, m), 4.73–4.65 (2H, m), 4.39 (2H, s), 3.32–3.34 (2H, m), 3.27 (2H, t).

Example 8

[6—chloro-2-[(2,3-dihydro-1-benzofuran-5-yl)carbonyl]-1H-indol-3-yl]acetic acid

The title compound was prepared according to the procedure described in Example 2 from methyl [6-chloro-2-[(2,3-dihydro-1-benzofuran-5-yl)carbonyl]-1Hindol-3-yl]acetate(Example 7).

m.p.: 217° C.

IR (KBr): 3368, 1699, 1618, 1605, 1578, 1570, 1541, 1329, 1265, 1250, 1097, 1059, 939 cm$^{-1}$.

$^1$H-NMR (DMSO-d$_6$) δ: 11.73 (1H, br s), 7.70–7.59 (3H, m), 7.47–7.46 (1H, m), 7.12 (1H, dd, 8.59 Hz, 1.81 Hz), 6.92 (1H, d, 8.24 Hz), 4.67 (2H, t, 8.72), 3.78 (2H, s), 3.26 (2H, t, 8.72 Hz).

Example 9

Methyl [2-[(1,3-benzodioxol-5-yl)carbonyl]-6—chloro-1H-indol-3-yl]acetate

The title compound was prepared according to the procedure described in step 2 of Example 1 from 5-bromoacetyl-1,3-benzodioxole (*J.Med. Chem.*, 1977, 20, 394) and methyl trans-4-chloro-2-[(phenylsulfonyl)amino]cinnamate (Example 1, step 1).

$^1$H-NMR (CDCl$_3$) δ: 8.85 (1H, br s), 7.68–7.55 (2H, m), 7.49–7.30 (3H, m), 7.17– 6.87 (2H, m), 6.09 (2H, s), 3.87 (2H, s), 3.68 (3H, s), 3.36 (2H, s).

Example 10

[2-[(1,3-benzodioxol-5-yl)carbonyl]-6-chloro-1H-indol-3-yl]acetic acid

The title compound was prepared according to the procedure described in Example 2 from methyl [2-[(1,3-benzodioxol-5-yl)carbonyl]-6-chloro-1H-indol-3-yl]acetate (Example 9).

MS (EI) m/z: 357 (M$^+$).

$^1$H-NMR (DMSO-d$_6$) δ: 11.73 (1H, br s), 7.72–7.46 (4H, m), 7.14–6.97 (2H, m), 6.18 (2H, s), 3.81 (2H, s).

Example 11

Methyl [5,6-dichloro-2-[(indan-5-yl)carbonyl]-1H-indol-3-yl]acetate

Step 1. Methyl trans-4,5-dichloro-2-nitrocinnamate

A mixture of 4,5-dichloro-2-nitrobenzaldehyde (J. Kenneth et al., *J.Med. Chem.*, 1968, 11, 946, 8.1 g, 37.0 mmol) and triphenylphophoranylidene acetate (13.0 g, 39.0 mmol) in toluene (200 ml) was heated at reflux temperature for 2 h. The mixture was concentrated and the crystalline residue was purified by flash column chromatography eluting with ethyl acetate/hexane (1:4) to afford 6.5 g (64%) of the title compound as white solids.

¹H-NMR (CDCl₃) δ: 8.20 (1H, s), 8.04 (1H, d, J=15.8 Hz), 7.72 (1H, s), 6.36 (1H, d, J=15.8 Hz).

Step 2. Methyl trans-2-amino-4,5-dichlorocinnamate

A mixture of methyl trans-4,5-dichloro-2-nitrocinnamate (step 1, 6.5 g, 24.0 mmol), iron powder (6.7 g, 120 mmol), ammonium chloride (600 mg, 12.0 mmol), ethanol (130 ml) and water (30 ml) was heated at reflux temperature for 2 h. The mixture was cooled and filtered through a pad of Celite. The filtrate was concentrated. The residue was diluted with ethyl acetate (200 ml) and washed with water (100 ml×2). After drying (MgSO₄), removal of solvent gave 5.3 g (90%) of the title compound as yellow solids.

¹H-NMR (CDCl₃) δ: 7.65 (1H, d, J=15.8 Hz), 7.42 (1H, s), 7.26 (1H, s), 6.81 (1H, s), 6.28 (1H, d, J=15.8 Hz).

Step 3. Methyl trans-4,5-dichloro-2-[(phenylsulfonyl)amino]cinnamate

The title compound was prepared according to the procedure described in step 1 of Example 1 from methyl trans-2-amino-4,5-dichlorocinnamate (step 2).

¹H-NMR (CDCl₃) δ: 7.80–7.70 (2H, m), 7.60–7.40 (6H, m), 7.02 (1H, br s), 6.13 (1H, d, J=16.1 Hz), 3.79 (3H, s).

Step 4. Methyl [5,6-Dichloro-2-[(indan-5-yl)carbonyl]-1H-indol-3-yl]acetate

The title compound was prepared according to the procedure described in step 2 of Example 1 from 5-bromoacetylindan* and methyl trans-4,5-dichloro-2-[(phenylsulfonyl)amino]cinnamate (step 3).

¹H-NMR (CDCl₃) δ: 9.01 (1H, br s), 7.72 (1H, s), 7.64 (1H, br), 7.57 (1H. br d, J=7.7 Hz), 7.50 (1H, s), 7.33 (1H, br d, J=7.7 Hz), 3.80 (2H, s), 3.68 (3H, s), 3.05–2.85 (4H, m), 2.21–2.08 (2H, m).

5-bromoacetylindan

To a solution of 5-acetylindan (500 mg, 3.1 mmol) in dichloromethane-methanol (2:1, 15 ml) was added tetrabutylammonium tribromide (1.64 g, 3.4 mmol) was added at room temperature. After 23 h, the mixture was concentrated and the residue was partitioned between diethyl ether (50 ml) and water (50 ml). The organic layer was separated and washed with water (50 ml), brine (50 ml), and dried (MgSO₄). Removal of solvent gave 698 mg (56%) of the title compound as white solids.

¹H-NMR (CDCl₃) δ: 7.83 (1H, br), 7.77 (1H, dd, J=1.6, 7.9 Hz, 1H), 7.32 (d, J=7.9 Hz, 1H), 4.44 (2H, s), 2.97 (t, J=7.6 Hz, 4H), 2.13 (quint, J=7.6 Hz, 2H).

Example 12

[5,6-dichloro-2-[(indan-5-yl)carbonyl]-1H-indol-3-yl]acetic acid

The title compound was prepared according to the procedure described in Example 2 from methyl [5,6-dichloro-2-[(indan-5-yl)carbonyl]-1H-indol-3-yl]acetate (Example 11)

MS (EI) m/z: 387 (M⁺).

IR (KBr): 3356, 2957, 2841, 1707, 1610, 1423, 1256, 1095, 866 cm⁻¹.

¹H-NMR (acetone-d₆) δ: 10.97 (1H, br s), 10.85 (1H, br s), 7.98 (1H, s), 7.74 (1H, s), 7.67 (1H, s), 7.60 (1H, d, J=7.4 Hz), 7.38 (1H, d, J=7.4 Hz), 3.93 (2H, s), 3.03–2.91 (4H, m), 2.11 (2H, quint, J=7.4 Hz).

Example 13

Methyl [5-methoxy-2-[(1,2,3,4-tetrahydroquinolin-7-yl)carbonyl]-1H-indol-3-yl]acetate Step 1. Methyl trans-5-methoxy-2-nitrocinnamate The title compound was prepared according to the procedure described in step 1 of Example 11 from 5-methoxy-2-nitrobenzaldehyde.

¹H-NMR (CDCl₃) δ: 8.21 (1H, d, J=15.8 Hz), 8.16–8.12 (1H, m), 7.00–6.96 (2H, m), 6.30 (1H, d, J=15.8 Hz), 3.93 (3H, s), 3.83 (3H, s).

Step 2. Methyl trans-5-methoxy-2-aminocinnamate

The title compound was prepared according to the procedure described in step 2 of Example 11 from methyl trans-5-methoxy-2-nitrocinnamate (step 1).

¹H-NMR (CDCl₃) δ: 7.83 (1H, d, J=15.8 Hz), 6.92–6.91 (1H, m), 6.82 (1H, dd, J=8.7, 2.8 Hz), 6.66 (1H, d, J=8.7 Hz), 6.35 (1H, d, J=15.8 Hz), 3.80 (3H, s), 3.76 (3H, s).

Step 3. Methyl trans-5-methoxy-2-[(phenylsulfonyl)amino]cinnamate

The title compound was prepared according to the procedure described in step 1 of Example 1 from methyl trans-5-methoxy-2-aminocinnamate (step 2).

¹H-NMR (CDCl₃) δ: 7.67–7.64 (2H, m), 7.54–7.37 (4H, m), 7.24 (1H, d, J=8.7 Hz), 6.95 (1H, d, J=2.8 Hz), 6.89 (1H, dd, J=8.7, 2.8 Hz), 6.82 (1H, br s), 6.10 (1H, d, J=15.8 Hz), 3.81 (3H, s), 3.77 (3H, s).

Step 4. Methyl [5-methoxy-2-[(1-ethoxycarbonyl-1,2,3,4-tetrahydroquinolin-7-yl)carbonyl]-1H-indol-3-yl]acetate The title compound was prepared according to the procedure described in step 2 of Example 1 from 7-bromoacetyl-1-ethoxycarbonyl-1,2,3,4-tetrahydroquinoline* and methyl trans-5-methoxy-2-[(phenylsulfonyl)amino]cinnamate (step 3).

¹H-NMR (CDCl₃) δ: 8.77 (1H, br s), 7.93 (1H, d, J=8.6 Hz), 7.63 (1H, dd, J=2.2, 8.6 Hz), 7.60 (1H, br), 7.34–7.28 (1H, m), 7.04 (1H, dd, J=2.5, 8.8 Hz), 7.01 (1H, br), 4.29 (2H, q, J=7.1 Hz), 3.93 (2H, s), 3.86 (3H, s), 3.86–3.73 (2H, m), 3.69 (3H, s), 2.81 (2H, t, J=6.5 Hz), 1.98 (1H, tt, J=6.3, 6.3 Hz), 1.36 (3H, t, J=7.1 Hz).

*7-bromoacetyl-1-ethoxycarbonyl-1,2,3,4-tetrahydroquinoline was prepared from 7-acetyl-1-ethoxycarbonyl-1,2,3,4-tetrahydroquinoline (Y.Ishihara et al., *J.Chem.Soc.Perkin Trans.* 1, 1992, 3401) according to the procedure for preparing 5-bromoacetylindan described in Example 11.

¹H-NMR (CDCl₃) δ: 7.94 (1H, d, J=8.6 Hz), 7.80–7.70 (2H, m), 4.41 (2H, s), 4.28 (2H, q, J=7.1 Hz), 3.84–3.76 (2H, m), 2.87–2.79 (2H, m), 2.30–1.91 (2H, m), 1.35 (3H, t, J=7.1 Hz).

Step 5. [5-Methoxy-2-[(1,2,3,4-tetrahydroquinolin-7-yl)carbonyl]-1H-indol-3-yl]acetic acid The title compound was prepared according to the procedure described in Example 2 from methyl [5-methoxy-2-[(1-ethoxycarbonyl-1,2,3,4-tetrahydroquinolin-7-yl)carbonyl]-1H-indol-3-yl]acetate (step 4).

MS (ESI) m/z: 365.13 (MH⁺).

IR (KBr): 3341, 2932, 1703, 1614, 1521, 1448, 1325, 1272, 1217, 1130 cm⁻¹.

¹H-NMR (acetone -d₆) δ: 11.85 (1H, br s), 10.62 (1H, br s), 7.66–7.55 (2H, m), 7.43 (1H, d, J=8.9 Hz), 7.18 (1H, d, J=2.5 Hz), 6.98 (1H, dd, J=2.5, 8.9 Hz), 6.57 (1H, d, J=9.2 Hz), 6.25 (1H, br s), 3.91 (2H, s), 3.85 (3H, s), 3.40 (2H, br t, J=5.8 Hz), 2.77 (2H, br t, J=5.8 Hz), 1.98–1.86 (2H, m).

Example 14

Step 1. Methyl [5,6-dichloro-2-[(1-ethoxycarbonyl-2,3-dihydro-1H-indol-5-yl)Carbonyl]-1H-indol-3-yl]acetate The title compound was prepared according to the procedure described in step 2 of Example 1 from methyl trans-4,5-dichloro-2-[(phenylsulfonyl)amino]cinnamate (Example 11, step 3) and 5-bromoacetyl-1-ethoxycarbonyl-2,3-dihydro-1H-indole*.

MS (EI) m/z: 474 (M$^+$).

$^1$H-NMR (CDCl$_3$) δ: 8.89 (1H, br s), 7.74–7.62 (4H, m), 7.54 (1H, s), 4.33 (2H, br q, J=7.4 Hz), 4.11 (2H, t, J=9.2 Hz), 3.82 (2H, s), 3.70 (3H, s), 3.18 (2H, t, J=9.2 Hz), 1.39 (3H, t, J=7.4 Hz).

*5-bromoacetyl-1-ethoxycarbonyl-2,3-dihydro-1H-indole was prepared from 5-acetyl-1-ethoxycarbonyl-2,3-dihydro-1H-indole (Y. Ishihara et al., *J.Chem.. Soc. Perkin Trans.*1, 1992, 3401) according to the procedure for preparing 5-bromoacetylindan described in Example 11.

$^1$H-NMR (CDCl$_3$) δ: 7.88–7.78 (3H, m), 4.41 (2H, s), 4.38–4.26 (2H, m), 4.08 (2H, t, J=9.2 Hz), 3.17 (2H, t, J=9.2 Hz), 1.37 (3H, t, J=7.1 Hz).

Step 2. [5,6-dichloro-2-[(2,3-dihydro-1H-indol-5-yl)carbonyl]-1H-indol-3-YL]Acetic acid The title compound was prepared according to the procedure described in Example 2 from methyl [5,6-dichloro-2-[(1-ethoxycarbonyl-2,3-dihydro-1H-indol-5yl)carbonyl]-1H-indol-3-yl]acetate (step 1).

MS (ESI) m/z: 389.08 (MH$^+$).

IR (KBr): 3279, 2882, 1709, 1620, 1595, 1535, 1448, 1326, 1267, 1200, 1107 cm$^{-1}$.

$^1$H-NMR (DMSO-d$_6$) δ: 11.80 (1H, br s), 7.91 (1H, s), 7.62 (1H, s), 7.52–7.45 (2H, m), 6.71 (1H, s), 6.50 (1H, d, J=8.7 Hz), 3.77 (2H, s), 3.60 (2H, br t, J=8.4 Hz), 3.00 (2H, br t, J=8.4 Hz).

Example 15

Methyl [6—chloro-2-[(2-methyl-1,2,3,4-tetrahydroisoquinolin-7-yl)carbonyl]-1H-indol-3-yl]acetate The title compound was prepared according to the procedure described in step 2 of Example 1 from 7-bromoacetyl-2-methyl-1,2,3,4-tetrahydroisoquinoline* and methyl trans-4-chloro-2-[(phenylsulfonyl)amino]cinnamate (Example 1, step 1).

MS (EI) m/z : 396 (M$^+$).

*7-bromoacetyl-2-methyl-1,2,3,4-tetrahydroisoquinoline was prepared from 7-acetyl-2-methyl-1,2,3,4-tetrahydroisoquinoline (P.Charpentier et al., *Tetrahedron*, 1996, 52, 10441) according to the procedure for preparing 3-bromoacetyl-5,6,7,8-tetrahydroisoquinoline described in Example 1.

Example 16

[6—chloro-2-[(2-methyl-1,2,3,4-tetrahydroisoquinolin-7-yl)carbonyl]-1H-indol-3-yl] acetic acid The title compound was prepared according to the procedure described in Example 2 from methyl [6-chloro-2-[(2-methyl-1,2,3,4-tetrahydroisoquinolin-7-yl)carbonyl]-1H-indol-3-yl]acetate (Example 15).

MS (FAB) m/z: 383 (MH $^+$).

The chemical structures of the compounds prepared in the Examples 1 to 16 are summarized in the following table.

TABLE

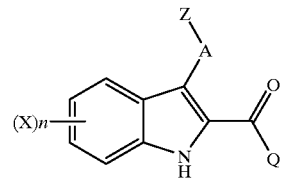

(Ia)

wherein A is CH$_2$; Z is C(=O)R$^2$; Q is

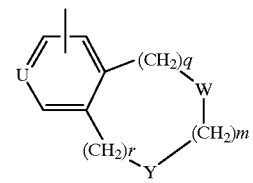

| Ex. # | (X)$_n$ | Z | Q |
|---|---|---|---|
| 1 | 6-Cl | C(=O)OCH$_3$ | 5,6,7,8-tetrahydroisoquinolin-3-yl |
| 2 | 6-Cl | C(=O)OH | 5,6,7,8-tetrahydroisoquinolin-3-yl |
| 3 | 6-Cl | C(=O)OCH$_3$ | 2,3-dihydro-1,4-benzodioxin-6-yl |
| 4 | 6-Cl | C(=O)OH | 2,3-dihydro-1,4-benzodioxin-6-yl |
| 5 | 5-CF$_3$ | C(=O)OCH$_3$ | 2,3-dihydro-1,4-benzodioxin-6-yl |
| 6 | 5-CF$_3$ | C(=O)OH | 2,3-dihydro-1,4-benzodioxin-6-yl |
| 7 | 6-Cl | C(=O)OCH$_3$ | 2,3-dihydro-1-benzofuran-5-yl |
| 8 | 6-Cl | C(=O)OH | 2,3-dihydro-1-benzofuran-5-yl |
| 9 | 6-Cl | C(=O)OCH$_3$ | 1,3-benzodioxol-5-yl |
| 10 | 6-Cl | C(=O)OH | 1,3-benzodioxol-5-yl |
| 11 | 5,6-diCl | C(=O)OCH$_3$ | indan-5-yl |
| 12 | 5,6-diCl | C(=O)OH | indan-5-yl |
| 13 | 5-CH$_3$O | C(=O)OH | 1,2,3,4-tetrahydroquinolin-7-yl |
| 14 | 5,6-diCl | C(=O)OH | 2,3-dihydro-1H-indol-5-yl |
| 15 | 6-Cl | C(=O)OCH$_3$ | 2-methyl-1,2,3,4-tetrahydro-isoquinolin-7-yl |
| 16 | 6-Cl | C(=O)OH | 2-methyl-1,2,3,4-tetrahydro-isoquinolin-7-yl | wherein A is CH$_2$; Z is C(=O)R$^2$; Q is

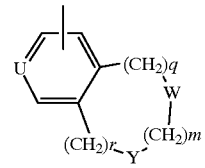

What is claimed is:

1. A compound of the following formula:

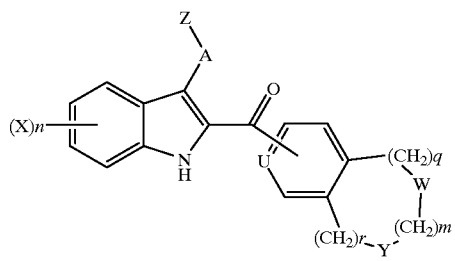

(I)

or a pharmaceutically acceptable salt thereof wherein
A is C$_{1-6}$ alkylene or —NR$^1$—;
Z is C(=L)R$^2$, or SO$_2$R$^3$;

U is CH or N;

W and Y are independently selected from —CH$_2$—, O, S and —N—R$^1$;

m is 1, 2 or 3;

q and r are independently 0, 1 or 2;

X is independently selected from halogen, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino and cyano;

n is 0, 1, 2, 3 or 4;

L is oxygen or sulfur;

R$^1$ is hydrogen or C$_{1-4}$ alkyl;

R$^2$ is hydroxy, C$_{1-6}$alkyl, halo-substituted C$_{1-6}$ alkyl, C$_{1-6}$ alkoxy, halo-substituted C$_{1-6}$ alkoxy, C$_{3-7}$ cycloalkoxy, C$_{1-4}$ alkyl(C$_{3-7}$ cycloalkoxy), —NR$^4$R$^5$, C$_{1-4}$ alkylphenyl-O— or phenyl-O—, said phenyl being optionally substituted with one to five substituents independently selected from halogen, C$_{1-4}$ alkyl, hydroxy, C$_{1-4}$ alkoxy and nitro;

R$^3$ is C$_{1-6}$ alkyl or halo-substituted C$_{1-6}$ alkyl; and

R$^4$ and R$^5$ are independently selected from hydrogen, C$_{1-6}$ alkyl and halo-substituted C$_{1-6}$ alkyl.

2. A compound according to claim 1, wherein

A is C$_{1-6}$ alkylene;

Z is C(=L)R$^2$;

U is CH or N;

W and Y are independently selected from —CH$_2$—, O, S and —N—R$^1$;

m is 1, 2 or 3;

q and r are independently 0, 1 or 2;

X is independently selected from halogen, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino and cyano;

n is 0, 1, 2 or 3;

L is oxygen or sulfur,

R$^1$ is hydrogen or C$_{1-4}$ alkyl;

R$^2$ is hydroxy, C$_{1-6}$ alkoxy, halo-substituted C$_{1-6}$ alkoxy, C$_{3-7}$ cycloalkoxy, C$_{1-4}$ alkyl(C$_{3-7}$ cycloalkoxy), —NR$^4$R$^5$, C$_{1-4}$ alkylphenyl-O— or phenyl-O—, said phenyl being optionally substituted with one to five substituents independently selected from halogen, C$_{1-4}$ alkyl, hydroxy, C$_{1-4}$ alkoxy and nitro; and R$^4$ and R$^5$ are independently selected from hydrogen, C$_{1-6}$ alkyl and halo-substituted C$_{1-6}$ alkyl.

3. A compound according to claim 1, wherein

A is C$_{1-4}$ alkylene;

Z is C(=O)R$^2$;

U is CH or N;

W and Y are independently selected from —CH$_2$—, O and —N—R$^1$;

m is 1 or 2;

q and r are independently 0 or 1;

X is independently selected from halogen, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino and cyano;

n is 1 or 2;

R$^1$ is hydrogen or C$_{1-4}$ alkyl; and

R$^2$ is hydroxy, C$_{1-6}$ alkoxy, halo-substituted C$_{1-6}$ alkoxy, C$_{3-7}$ cycloalkoxy, C$_{1-4}$ alkyl(C$_{3-7}$ cycloalkoxy), C$_{1-4}$ alkylphenyl-O— or phenyl-O—, said phenyl being optionally substituted with one to five substituents independently selected from halogen, C$_{1-4}$ alkyl, hydroxy, C$_{1-4}$ alkoxy and nitro.

4. A compound according to claim 1, wherein

A is methylene or ethylene;

Z is C(=O)R$^2$;

U is CH or N;

W and Y are independently selected from —CH$_2$—, O and —N—R$^1$;

m is 1 or 2;

q and r are independently 0 or 1;

X is independently selected from fluoro, chloro, C$_{1-4}$ alkyl, halo-substitutedmethyl, and methoxy;

n is 1 or 2;

R$^1$ is hydrogen or methyl; and

R$^2$ is hydroxy or C$^{1-6}$ alkoxy;

with the proviso that at least one of U, W and Y is a hetero atom.

5. A compound according to claim 1, wherein

A is methylene;

Z is C(=O)OH;

U is CH or N;

W and Y are independently selected from —CH$_2$—, O, and —N—R$^1$;

m is 1, or 2;

q and r are independently 0 or 1;

X is independently selected from chloro, trifluoromethyl, and methoxy;

n is 1 or 2; and

R$^1$ is hydrogen or methyl.

6. A compound according to claim 1, wherein

A is methylene;

Z is C(=O)OH;

U is CH or N;

W, Y, m, q and r are selected from the group consisting of
 a) W and Y are —CH$_2$—, m is 1, and q and r are independently 0 or 1;
 b) W and Y are —CH$_2$—, m is 2, and q and r are 0;
 c) W and Y are O, m is 1 or 2, and q and r are 0;
 d) W is —CH$_2$—, Y is O, m is 1, and q and r are 0;
 e) W is O, Y is —CH$_2$—, m is 1, and q and r are 0;
 f) W is —N—R$^1$, Y is —CH$_2$—, m is 1, and q and r are independently 0 or 1;
 g) W is —N—R$^1$, Y is —CH$_2$—, m is 2, and q and r are 0;
 h) W is —CH$_2$—, Y is —N—R$^1$, m is 1, and q and r are independently 0 or 1;
 i) W is —CH$_2$—, Y is —N—R$^1$, m is 2, and q and r are 0;

X is independently selected from chloro, trifluoromethyl, and methoxy;

n is 1 or 2; and

R$^1$ is hydrogen or methyl.

7. A compound according to claim 1 selected from

[6-chloro-2-[(5,6,7,8-tetrahydroisoquinolin-3-yl)carbonyl]-1H-indol-3-yl]acetic acid;

[6-chloro-2-[(2,3-dihydro-1,4-benzodioxin-6-yl)carbonyl]-1H-indol-3-yl]acetic acid;

[2-[(2,3-dihydro-1,4-benzodioxin-6-yl)carbonyl]-5-trifluoromethyl-1H-indol-3-yl]acetic acid;

[6-chloro-2-[(2,3-dihydro-1-benzofuran-5-yl)carbonyl]-1H-indol-3-yl]acetic acid;

[2-[(1,3-benzodioxol-5-yl)carbonyl]-6-chloro-1H-indol-3-yl]acetic acid;

[5,6-dichloro-2-[(indan-5-yl)carbonyl]-1H-indol-3-yl]acetic acid;

[5-methoxy-2-[(1,2,3,4-tetrahydroquinolin-7-yl)carbonyl]-1H-indol-3-yl]acetic acid;

[5,6-dichloro-2-[(2,3-dihydro-1H-indol-5-yl)carbonyl]-1H-indol-3-yl]acetic acid; and

[6-chloro-2-[(2-methyl-1,2,3,4-tetrahydroisoquinolin-7-yl)carbonyl]-1H-indol-3-yl]acetic acid, and a salt thereof.

8. A compound according to claim 7, selected from

[6-chloro-2-[(5,6,7,8-tetrahydroisoquinolin-3-yl)carbonyl]-1H-indol-3-yl]acetic acid;

[6-chloro-2-[(2,3-dihydro-1,4-benzodioxin-6-yl)carbonyl]-1H-indol-3-yl]acetic acid;

[2-[(2,3-dihydro-1,4-benzodioxin-6-yl)carbonyl]-5-trifluoromethyl-1H-indol-3-yl]acetic acid; and

[6-chloro-2-[(2,3-dihydro-1-benzofuran-5-yl)carbonyl]-1H-indol-3-yl]acetic acid;

and a salt thereof.

9. A compound according to claim 1, wherein

A is methylene;

Z is C(=O)OCH$_3$;

U is CH or N;

W and Y are independently selected from —CH$_2$—, O and N—R$^1$;

m is 1, or 2;

q and r are independently 0 or 1;

X is independently selected from chloro, trifluoromethyl, and methoxy;

n is 1 or 2; and

R$^1$ is hydrogen or methyl.

10. A compound according to claim 9 selected from methyl [6-chloro-2-[(5,6,7,8-tetrahydroisoquinolin-3-yl)carbonyl]-1H-indol-3-yl]acetate;

methyl [6-chloro-2-[(2,3-dihydro-1,4-benzodioxin-6-yl)carbonyl]-1H-indol-3-yl]acetate;

methyl [2-[(2,3-dihydro-1,4-benzodioxin-6-yl)carbonyl]-5-trifluoromethyl-1H-indol-3-yl]acetate;

methyl [6-chloro-2-[(2,3-dihydro-1-benzofuran-5-yl)carbonyl]-1H-indol-3-yl]acetate;

methyl [2-[(1,3-benzodioxol-5-yl)carbonyl]-6-chloro-1H-indol-3-yl]acetate;

methyl [5,6-dichloro-2-[(indan-5-yl)carbonyl]-1H-indol-3-yl]acetate; and methyl [6-chloro-2-[(2-methyl-1,2,3,4-tetrahydroisoquinolin-7-yl)carbonyl]-1H-indol-3-yl]acetate, and a salt thereof.

11. A pharmaceutical composition useful for the treatment of a medical condition in which prostaglandins are implicated as pathogens, which comprises a compound of the formula (I) of claim 1, and a pharmaceutically inert carrier.

12. A method for the treatment of a medical condition in which prostaglandins are implicated as pathogens, in a mammalian subject, which comprises administering to said pharmaceutical composition according to claim 1.

* * * * *